US011898180B2

(12) United States Patent
Lau et al.

(10) Patent No.: US 11,898,180 B2
(45) Date of Patent: Feb. 13, 2024

(54) COMPOSITIONS AND METHODS FOR AMINO ACID DEPLETION THERAPY

(71) Applicant: AVALON POLYTOM (HK) LIMITED, Central (HK)

(72) Inventors: Johnson Yiu-Nam Lau, Houston, TX (US); Yun Chung Leung, Shatin (HK); Kuo-Ming Yu, Taipei (TW); Yuk-Keung Yeung, Kwai Chung (HK); Pui Shi Pang, Kowloon (HK); Qui-Lim Choo, El Cerrito, CA (US)

(73) Assignee: Avalon Polytom (HK) Limited, Central (HK)

( * ) Notice: Subject to any disclaimer, the term of this patent is extended or adjusted under 35 U.S.C. 154(b) by 268 days.

(21) Appl. No.: 16/639,078

(22) PCT Filed: Aug. 16, 2018

(86) PCT No.: PCT/US2018/000208
§ 371 (c)(1),
(2) Date: Feb. 13, 2020

(87) PCT Pub. No.: WO2019/035935
PCT Pub. Date: Feb. 21, 2019

(65) Prior Publication Data
US 2021/0189370 A1      Jun. 24, 2021

Related U.S. Application Data

(60) Provisional application No. 62/546,489, filed on Aug. 16, 2017, provisional application No. 62/591,102, filed on Nov. 27, 2017.

(51) Int. Cl.
*C12N 9/78* (2006.01)
*C07K 1/18* (2006.01)

(52) U.S. Cl.
CPC ............... *C12N 9/78* (2013.01); *C07K 1/18* (2013.01); *C12Y 305/03001* (2013.01)

(58) Field of Classification Search
None
See application file for complete search history.

(56) References Cited

U.S. PATENT DOCUMENTS

| 2010/0111925 A1 | 5/2010 | Georgiou et al. |
| 2010/0247508 A1 | 9/2010 | Leung |
| 2015/0010522 A1 | 1/2015 | Cheng et al. |

FOREIGN PATENT DOCUMENTS

| CN | 103184208 | 7/2013 |
| EP | 2799539 | 12/2012 |
| JP | H02117383 A | 5/1990 |
| JP | 2012531893 A | 12/2012 |
| JP | 2015503333 A | 2/2015 |
| JP | 2012521201 A | 7/2015 |
| WO | 2005010195 | 2/2005 |
| WO | 2013097567 | 7/2013 |

OTHER PUBLICATIONS

Kuo et al. (Pharm. vol. 14:72, 2021, pp. 1-20).*
Fung et al. (J. of Hemat. & Oncol., 10:144, 2017, pp. 1-18).*
Krall (Nature Comm., vol. 10, Sep. 2015, pp. 1-13).*
Lukey et al. (Drug Discovery, vol. 22, No. 5, May 2017, pp. 796-804).*
Chou (2010, Cancer Research, vol. 70(2), pp. 440-446).*
Fung et al. (2017,J. of Hemat. & Oncology, 10:144, pp. 1-18).*
Chou, Ting-CHao. "Frequently asked questions in drug combinations and the mass-action law-based answers," Molecular Pharmacology & Chemistry Program. Synergy 1, Jul. 3-21, 2014. 19 pages.
Fee, et al. "Purification of Pegylated Proteins," Protein Purification Principles. Third Edition. 2011. 24 pages.
Fultang, et al. "Molecular basis and current strategies of therapeutic arginine depletion for cancer," International Journal of Cancer. 139, 501-509. 2016. 9 pages.
Fung, et al. "Drug-induced amino acid deprivation as strategy for cancer therapy," Journal of Hematology and Oncology. 10:144. 2017. 18 pages.
Hensley, et al. "Glutamine and cancer: cell biology, physiology, and clinical opportunities," The Journal of Clinical Investigation. vol. 123, No. 9. Sep. 2013. 8 pages.
Yu, et al. "Rational design, engineer, and characterization of a novel pegylated single, isomer human arginase for arginine depriving anti-cancer treatment," Life Sciences. Sep. 2020. 11 pages.
Extended European Search Report dated Mar. 30, 2021, from related EP application No. 18846415.0. 17 pages.
PCT Search Report & Written Opinion (ISA/KR) dated Jan. 21, 2019 for PCT/US2018/000208 in the name of Avalon Polytom (HK) Limited filed on Aug. 16, 2018 (18 pages).
Rachel A. Egler et al, L-asparaginase in the treatment of patients with acute lymphoblastic leukemia; downloaded for free from http://www.jpharmacol.com on Thursday, Jan. 3, 2019, IP: 1.245.161.220 (10 pages).

(Continued)

*Primary Examiner* — Hope A Robinson
(74) *Attorney, Agent, or Firm* — Fish IP Law, LLP

(57) ABSTRACT

Compositions and methods for the preparation of high purity arginase and high efficiency preparation of monosubstituted polyethylene glycol conjugation of arginase are provided, as are methods for using arginase in combination with asparaginase to inhibit cancer cells. High purity arginase is provided by applying an initial high temperature precipitation step, followed by ion exchange to provide arginase at a purity of 90% or greater. Conjugation with either linear or branched polyethylene glycol is performed using a maleimide-derivatized polyethylene glycol at low molar excess relative to arginase and at reduced temperature. Such polyethylene glycol-derivatized arginase is useful in combination with asparaginase in inhibiting the growth of cancer cells, particularly cells that have low endogenous asparaginase expression.

4 Claims, 13 Drawing Sheets
Specification includes a Sequence Listing.

(56) References Cited

OTHER PUBLICATIONS

Ezima Esther Nkechi et al, Purification and Characterization of Fruit Bat (*Eidolon helvum kerr*) Liver Arginase; International Journal of Biological Chemistry 1 (1): 11-20, 2007 (10 pages).
Wise, et al. "Glutamine addiction: a new therapeutic target in cancer," Cell. 8 pages.

\* cited by examiner

COMPOSITIONS AND METHODS FOR AMINO ACID DEPLETION THERAPY

This application claims the benefit of U.S. Provisional Application No. 62/546,489, filed Aug. 16, 2017 and U.S. Provisional Application No. 62/591,102, filed Nov. 27, 2017. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is arginase purification, arginase modification, and medical uses of arginase and asparaginase.

BACKGROUND

The following description includes information that may be useful in understanding the present invention. It is not an admission that any of the information provided herein is prior art or relevant to the presently claimed invention, or that any publication specifically or implicitly referenced is prior art.

There is growing evidence suggesting that amino acid deprivation can be a potent candidate for treating cancers. The deprivation of specific amino acids (such as arginine, asparagine, or glutamine) has found to be useful for treating different types of cancers (Feun, You et al. 2008; Hensley, Wasti et al. 2013; Krall, Xu et al. 2016). All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. The effectiveness of amino acid deprivation is thought to be due to downstream effects such as the deactivation of mTORC1 and disruption of protein synthesis.

Application of recombinant human arginase (rhArg) to deplete arginine has been shown to be effective in inhibiting cancer cell growth in vitro (Lam, Wong et al. 2009; Tsui, Lam et al. 2009). Arginine was chosen as targeted amino acid not only because of its semi-essential role in protein synthesis, but also the role of arginine in activating mTORC1 (Carroll, Maetzel et al. 2016; Chantranupong, Scaria et al. 2016; Krall, Xu et al. 2016; Saxton, Chantranupong et al. 2016; Zheng, Zhang et al. 2016). It was found that arginine deprivation could effectively inhibit various cancers cell lines including cell lines derived from breast, colon, lung, and cervical cancers.

The enzyme arginase acts on arginine to produce ornithine and urea, and is part of the urea cycle. Arginase is finding increasing use as a chemotherapeutic agent, where it is utilized to decrease the concentration of arginine in serum. These depleted serum arginine levels can effectively "starve" cancer cells (many varieties of which are auxotrophic in regards to arginine).

Use of arginase as a therapeutic agent requires the availability of human arginase in both large quantities and high purity. Attempts have been made to provide highly purified recombinant human arginase. For example, U.S. Pat. No. 8,507,245 (to Leung and Lo) describes a pseudo-affinity chromatography method for purifying recombinant human arginase 1 that has been modified to provide a single site for PEGylation. The described method, however, is restricted to forms that include a poly-histidine sequence which permits complex formation with the metal pseudo-affinity media. This pseudo-affinity media is used in an affinity purification step necessitated by the use of a large excess of a reactive PEG analog in the conjugation reaction. As such the arginase 1 purified by such methods cannot be considered fully human without additional processing to remove the poly-histidine sequence.

Unmodified arginase is unstable in plasma, which severely limits its therapeutic applications. Many attempts have been explored to extend plasma half-life, including conjugation of the protein with the polymer polyethylene glycol (PEGylation). A widely used conjugation strategy is non-selective PEGylation of amino groups (for example, ε-amines of lysines) of the arginase, as described by U.S. Pat. No. 9,050,340 (to Georgiou and Stone). Such a process requires the use of a significant molar excess of costly amine-reactive PEG reagents, in part due to relatively rapid hydrolysis of such reagents. Such random conjugation also complicates qualitative and quantitative characterization of the modified arginase, which in turn limits its pharmaceutical use. Using such an approach consistent product quality is not likely to be achieved unless the coupling reaction is performed under very tightly controlled conditions, which are frequently not amenable to scaleup.

Thus, there is still a need for methodologies that can provide active and effectively and consistently PEGylated arginase at high purity.

SUMMARY OF THE INVENTION

The inventive subject matter provides compositions and methods for preparing and derivatizing high purity arginase, and utilizing arginase so prepared in combination with asparaginase in treating cancer.

One embodiment of the inventive concept is a method of purifying arginase, by obtaining a cell (such as a bacterial cell) that expresses arginase, disrupting the cell to produce a lysate comprising arginase, and increasing temperature of the lysate to a precipitating temperature (e.g. at least 50° C., or about 65° C.) in the presence of $CoCl_2$ (for example, at a concentration of at least 20 mM) for a period of time sufficient to precipitate contaminants from the lysate and produce a supernatant that includes a first partially purified arginase (e.g. about 5 to 30 minutes). This supernatant is contacted with an anion exchanger, which binds additional contaminates and provides a flow through fraction that includes a partially purified $Co^{2+}$-arginase (i.e. an arginase in which $Mn^{2+}$ is replaced with $Co^{2+}$). Such a partially purified $Co^{2+}$-arginase can have a purity of about 80% or higher.

In some embodiments the method includes the additional steps of contacting the flow through fraction with a cation exchanger to produce a bound fraction that includes the arginase and a second flow through fraction. An elution buffer is applied to the cation exchanger to elute a purified $Co^{2+}$-arginase. Such a purified $Co^{2+}$-arginase can have a purity of about 90% or higher. The arginase can be human arginase 1. Then anion and cation exchangers used can be strong ion exchangers.

Another embodiment of the inventive concept is a method of selectively derivatizing a protein (such as human arginase 1 or a mutation thereof), by obtaining a protein that includes at least one cysteine, contacting the protein with a PEG-maleimide in a buffer having a pH between 6.5 and 7.0 at a temperature of from 2° C. to 15° C., and incubating the protein with the PEG-maleimide for between 24 hours and 72 hours at 2° C. to 15° C. to produce a PEG-derivatized protein. In such a method the PEG-maleimide is present at less than a 4-fold molar excess over the protein. The PEG-maleimide can be derived from a branched or linear PEG. In some embodiments the protein in an arginase with a mutation that eliminates all but one cysteine. In some embodiments the protein does not include a poly-histidine sequence. In some embodiments the method includes the addition step of separating the PEG-derivatized protein from unreacted or hydrolyzed PEG-maleimide, for example by dialysis, size exclusion chromatography, and/or ion exchange chromatography.

Another embodiment of the inventive concept is a preparation of PEG-modified human arginase 1, which includes a peptide sequence corresponding to SEQ ID NO: 1 that is covalently coupled to a single PEG moiety having a molecular weight of at least 20 kDa. The PEG-modified human arginase 1 represents at least 90% of human arginase in such a preparation, and the PEG-modified human arginase 1 does not include a poly-histidine sequence. The PEG moiety of the PEG-modified human arginase can be linear or branched (for example, having a "Y" or "V" configuration). In some of such embodiments the PEG-modified human arginase 1 can include a metal cofactor, such as manganese, nickel, and/or cobalt.

Another embodiment of the inventive concept is a method of inhibiting a cancer cell, by reducing arginine concentration in a media utilized in culturing the cancer cell and reducing asparagine concentrations in the media. The arginine concentration can be reduced using an arginase (for example, a recombinant human arginase). Similarly, the asparagine concentration can be reduced using an asparaginase (ASNase). In some of such embodiments the cancer cell has low asparagine synthetase (ASNS) expression. In some of such embodiments the method includes the additional step of reducing glutamine concentration, for example using aminotransferase inhibitor (such as aminooxyacetate).

Another embodiment of the inventive concept is a composition for inhibiting a cancer cell, which includes an arginine reducing enzyme and an asparagine reducing enzyme. The arginine reducing enzyme can be an arginase, such as a recombinant human arginase. Similarly, the asparagine reducing enzyme can be an asparaginase (ASNase). In some of such embodiments the cancer cell has low asparagine synthetase (ASNS) expression. The composition can also include a compound that reduces glutamine concentration, such as an aminotransferase inhibitor (for example aminooxyacetate).

Various objects, features, aspects and advantages of the inventive subject matter will become more apparent from the following detailed description of preferred embodiments, along with the accompanying drawing figures in which like numerals represent like components.

DETAILED DESCRIPTION

Figure 2:
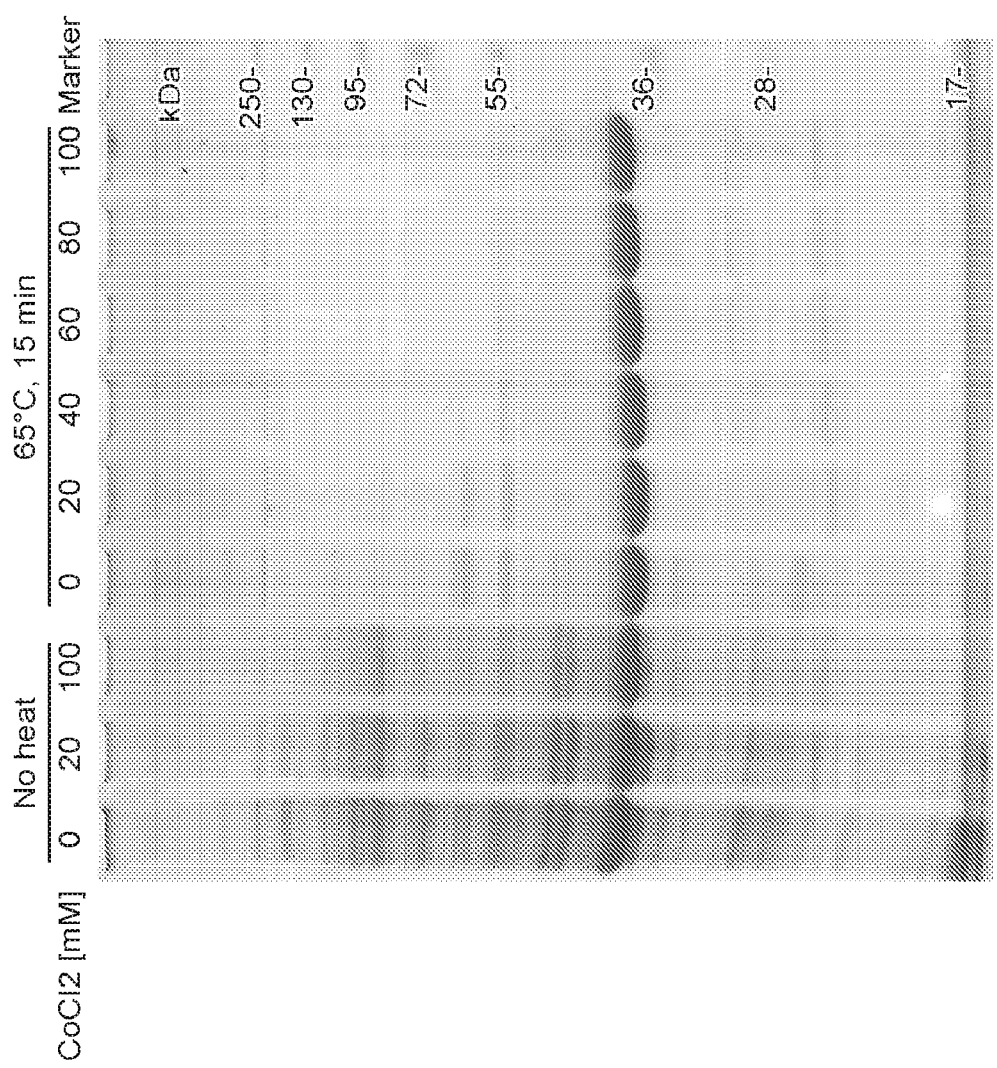
FIG. 2: A photograph of a electrophoresis gel showing results from reducing SDS-PAGE on an 8-16% gradient gel for homogenate and products of thermal precipitation.

The following description includes information that may be useful in understanding the present invention. It is not an admission that any of the information provided herein is prior art or relevant to the presently claimed invention, or that any publication specifically or implicitly referenced is prior art.

The inventive subject matter provides apparatus, compositions, and methods that provide scalable purification of human arginase. In compositions and methods of the inventive concept a preparation containing recombinant human arginase is incubated at an elevated temperature, which results in the formation of a precipitate. This precipitate is removed, and the supernatant collected and subjected to ion exchange on an anion exchanger. The flow through fraction from this anion exchange process is collected and subjected to a further polishing step on a cation exchanger, where human arginase is eluted using a salt gradient. The resulting human arginase can be modified, for example by PEGylation. Such PEGylation can be carried out using a relatively small molar excess of a reactive PEG analog at reduced temperatures in order to produce a PEGylated human arginase at high purity. The inventive subject matter provides apparatus, systems and methods in which compounds that reduce arginine and asparagine are used to inhibit the growth of cancer cells. Such compounds can be enzymes, such as arginase and/or asparaginase, which catalytically reduce the concentration of arginine and asparagine. In a preferred embodiment such enzymes are human enzymes, such a recombinant human arginase (rhArg).

Such amino acid depleting enzymes can be provided as enzymes purified from natural sources or as products of recombinant bacteria, fungi, plant cells, or animal cells. Enzymes utilized in such therapy can have a purity exceeding 80%, 85%, 90%, 95%, 98%. 99%, or higher, and may be modified post-translation. Such modifications can include modifications that improve absorption and/or half life (such as PEGylation). Enzyme-containing pharmaceutical preparations can be administered intravenously, for example by injection or infusion. Such preparations can include or be co-administered with chemotherapeutic agents utilized for cancer treatment, immunotherapeutic agents, and/or radiation therapy.

Various objects, features, aspects and advantages of the inventive subject matter will become more apparent from the following detailed description of preferred embodiments, along with the accompanying drawing figures in which like numerals represent like components.

One should appreciate that the disclosed techniques provide many advantageous technical effects, including scalable production of highly purified human arginase having a native sequence from recombinant sources.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In embodiments of the inventive concept, one of the amino acid depleting enzymes is an arginase, such as a mammalian, avian, reptilian, plant, fungal, and/or bacterial arginase. In some such embodiments the arginase can be a human arginase provided as a product of genetic engineering, for example of bacterial, yeast, fungal, insect, plant, or mammalian cells in culture. Such an arginase can include one or more sequence modifications that serve to improve the specificity of subsequent conjugation reactions, for example the removal or replacement of one or more amino acids containing potentially modifiable side chains. In a preferred embodiment a recombinant human arginase can be produced in an *E. coli* clone, for example strain BL21 (T7 Express from New England Biolabs) containing a kanamycin-resistant, expression vector pET-30a into which is inserted a cDNA encoding for human arginase 1. Culture of such a transformed *E. coli* can be performed at any suitable scale, for example 0.1 L, 1 L, 5 L, 10 L, or more in appropriate media. The optical density of such a bacterial culture can be monitored in order to determine when it has reached optimal density for collection of recombinant human arginase 1. Alternatively, culture can be permitted to continue for a pre-defined period of time prior to collection of the bacteria and further processing.

Figure 1:
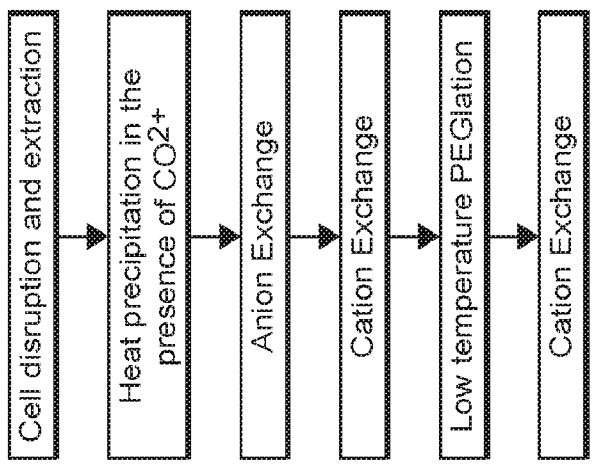
FIG. 1: A flow chart of an exemplary process of the inventive concept.

FIG. 1 provides a flow chart that outlines an example of a process of the inventive concept. As shown, bacteria or other cells expressing the human arginase 1 are collected, disrupted, and extracted in order to release the desired enzyme. Bacteria can be collected by any suitable means, including filtration, settling, and/or centrifugation. Optionally, bacteria thus collected can be rinsed or washed prior to subsequent processing.

Disruption of the bacteria or other cells can be performed by any suitable process. These include, but are not limited to, enzymatic digestion, osmotic shock, sudden pressure change (e.g. by expression through a press, and/or sonication). In some embodiments these processes can be carried out under temperature controlled conditions. For example, the temperature of bacteria or other cells undergoing sonication can be controlled to ensure that it does not exceed a temperature compatible with subsequent activity of human arginase. In other embodiments one or more protease inhibitors can be added prior to, during, or following disruption of the bacteria or other cells. In still other embodiments one or more stabilizers (for example, an anti-oxidant) can be added prior to, during or following disruption of the bacteria or other cells.

Following disruption of the bacteria or other cells, residual debris can be removed (e.g. by settling, filtration, and/or centrifugation) to leave a solution that includes the human arginase. Inventors have found that arginase is surprisingly stable at elevated temperatures (i.e. greater than 37° C., 40° C., 45° C., 500 C, 60° C., and/or 70° C.) that can result in denaturation and subsequent precipitation of undesirable contaminating proteins. For example, Inventors have found that human arginase I is stable at 74° C., a temperature that results in precipitation of many contaminating proteins. Without being limited to theory believe that this stability is provided by complex formation with divalent ions. This permits arginase to be extracted at elevated temperatures (i.e. temperatures in excess of 37° C.) in the presence of divalent ions, such as $Mn^{2+}$ or $Co^{2+}$, in order to produce a precipitate (which includes contaminating proteins) and a supernatant (which includes the human arginase) Moreover, because cobalt-chelated arginase presents a much enhanced catalytic activity ($k_{cat}/K_M$), $COCl_2$ can be utilized during extraction to not provide a high catalytic potential but also to replace $Mn^{2+}$ of the arginase with $Co^{2+}$. The temperature and incubation time can be selected to provide adequate to optimal recovery, purity, and activity of the human arginase.

Incubation temperature can range from about 400 C, 45° C., 500 C, 55° C., 600 C, 65° C., 700 C, 75° C., 80° C., 85° C., 90° C., or more than about 90° C. Incubation time can range from 1 minute, 2 minutes, 3 minutes, 5 minutes, 10 minutes, 15 minutes, 30 minutes, 45 minutes, 1 hour, 2 hours, 3 hours, 4 hours, 8 hours, 12 hours, or more than 12 hours. In some embodiments the temperature can be varied during the incubation period. In a preferred embodiment the incubation temperature is 65° C. and the incubation period is 15 minutes. Inventors have found that such methods can advantageously remove the majority of unwanted heat-sensitive proteins while simultaneously replacing $Mn^{2+}$ with $Co^{2+}$ in the arginase.

Following this precipitation step the supernatant, containing the arginase, is collected for further processing. The supernatant can be separated from the precipitate by any suitable method, including settling, filtration, and/or centrifugation. The collected supernatant is then transferred (for example, by dialysis, gel filtration, and/or diafiltration) to an aqueous buffer compatible with anion exchange. The composition of such a buffer is at least partially dependent on the nature of the anion exchange media used, but can generally have relatively low (e.g. less than 100 mM) molarity and an elevated pH (e.g. greater than 7). Such an anion exchanger can be a weak anion exchanger with a relatively low affinity for anions, such as an anion exchanger that includes an ammonium group. Alternatively, such an anion exchanger can be a strong anion exchanger with a relatively high affinity for anions (such as an anion exchanger that includes a quaternary amine group). In a preferred embodiment a strong anion exchanger is employed. For example, if a strong anion exchanger such as Capto Q™ is utilized a suitable buffer can be 20 mM Tris at pH 8.05. The final protein concentration of the supernatant can be adjusted to provide adequate to optimal separation of arginase from at least a portion of the contaminating materials present.

After being transferred to an appropriate anion exchange buffer, the supernatant is treated with an anion exchange medium. As noted above, such an anion exchange medium can be a strong anion exchange medium, for example an anion exchange medium that includes a fixed quaternary amine. The anion exchange medium can be provided in any suitable form, for example as a filter, an immiscible liquid, a porous particle, and/or a non-porous particle. An example of such a strong anion exchange medium is Capto Q™ media (GE Healthcare), which is provided as a porous particle and includes pendant quaternary amine groups. Such an anion exchange medium can be applied as a bulk solid phase that is mixed and/or suspended in the supernatant and then removed (for example, by settling, centrifugation, and/or filtration). In a preferred embodiment the anion exchange medium is provided as a chromatography bed in a chromatography column.

The supernatant can be applied to a bed of anion exchange medium, resulting in the binding of at least some contaminants to the media while permitting passage of a flow through fraction containing partially purified arginase. The volume and configuration of such a column, along with flow rate during application, can be optimized to provided adequate to optimal capture of contaminants from the supernatant. Following passage and collection of the partially purified human arginase the anion exchange medium can be rinsed and regenerated (for example, with a buffer containing a high salt concentration) for re-use. In such embodiments the anion exchange medium can be selected to tolerate sterilizing and/or pyrogen reducing treatments.

The collected partially purified arginase can be utilized as is (depending upon the application), or subjected to a further polishing step. It is likely that pharmaceutical usage will require such further processing. If a polishing step is desired the partially purified arginase can be transferred to an aqueous buffer suitable for cation exchange chromatography. This transfer can be accomplished by any suitable means, including dialysis, gel filtration, and/or diafiltration. In some embodiments this transfer can effectively be accomplished by dilution of the partially purified human arginase in a dilution buffer that provides a suitable cation exchange buffer composition. In still other embodiments the buffer utilized in the previous anion exchange step can be adjusted (for example, by manipulation of the pH and/or ionic strength) to be suitable for cation exchange.

When the partially purified arginase is in a suitable cation exchange buffer it can be applied to a cation exchange medium. Suitable buffers typically have low to moderate ionic strength (e.g. less than 200 mM) and neutral pH (e.g. pH 7). An example of a suitable cation exchange buffer is 50 mM Tris, pH 7. Such a cation exchanger can be a weak cation exchanger with a relatively low affinity for cations, such as a cation exchanger that includes a carboxyl group. Alternatively, such a cation exchanger can be a strong cation exchanger with a relatively high affinity for cations (such as a cation exchanger that includes a sulfonate group). In a preferred embodiment the cation exchange medium can be a strong cation exchange medium such as Capto S™ (GE Healthcare), which includes pendant sulfonate groups. Since arginase from the partially purified arginase preparation is bound to and selectively eluted from the cation exchange medium, the cation exchange medium is preferably provided as a solid (for example, a particle) that is fixed in place so as to support gradient elution. In a preferred embodiment the cation exchange medium is provided as a chromatography bed in a chromatography column. The volume and configuration of such a column, along with flow rate during application, can be optimized to provided adequate to optimal capture and subsequent release of human arginase from the cation exchange medium.

When using such a cation exchange column, a partially purified arginase that has been transferred into a cation exchange buffer is applied the column at a flow rate that permits capture of the arginase on the cation exchange medium. Following application of the partially purified arginase the cation exchange column can be rinsed with an additional volume of cation exchange buffer (for example, 1 to 10 column volumes) in order to remove unbound material. Optionally, UV absorbance can be monitored during this process in order to determine when washing is complete. In some embodiments an additional wash step can be used in which a more stringent cation exchange buffer (for example, a wash buffer with higher pH and/or ionic strength than the cation exchange buffer) is applied to the cation exchange column in order to displace loosely bound material. An example of such a wash buffer is 50 mM Tris+sodium chloride (NaCl) at less than 0.5 M, pH 7. In some embodiments a series of such wash buffers of varying stringency can be used.

Following application of the partially purified arginase and any subsequent washing steps, purified arginase is eluted from the cation exchange medium by application of an elution buffer. This elution can be provided by the application of an elution buffer of fixed composition as a single bolus, to provide a step elution. In other embodiments the elution buffer can be applied as a mixture with the cation exchange buffer, where the ratio of elution buffer to cation exchange buffer increases over time. In such a gradient elution approach the rate at which this ratio changes can be linear over time, or non-linear. In a preferred embodiment elution is accomplished using a linear gradient that transitions the composition of the column buffer from cation exchange buffer to elution buffer at a constant rate over time. The elution buffer can differ from the cation exchange buffer in pH, ionic strength, or both. In a preferred embodiment the elution buffer essentially duplicates the composition and pH of the cation exchange buffer, but additionally includes a high concentration (e.g. greater than 0.2 M) of NaCl. An example of such an elution buffer is 50 mM Tris+0.5M NaCl, pH 7.

During such a gradient elution the UV absorbance of material leaving the column can be monitored to determine which fraction should be collected. Fractions can be selected on the basis of arginase content and/or presence of contaminants in order to provide the desired yield and purity. Such fractions can be collected, pooled, and transferred to a buffer suitable for stability. In some embodiments such purified arginase can be subsequently frozen and/or lyophilized. In still other embodiments purified arginase obtained in such a manner can be derivatized, for example by PEGylation, for pharmaceutical use. Typical results of methods and compositions of the inventive concept can provide high purity (>90%) human arginase at yields of about 30%. Following passage and collection of the purified human arginase the cation exchange medium can be rinsed and regenerated (for example, with a buffer containing a high salt concentration) for re-use. In such embodiments the cation exchange medium can be selected to tolerate sterilizing and/or pyrogen reducing treatments.

In some embodiments, an arginase purified as described above can be subsequently chemically modified. Suitable chemical modifications include biotinylation, charge modification, crosslinking, and conjugation (such as grafting of hydrophilic polymers, e.g. dextran, PEG, etc.). Such a polymer can be grafted to the purified arginase through the use of reactive forms of the polymer, for example by contacting purified arginase with a polymer carrying an amine-reactive and/or thiol-reactive group. Suitable reactive groups include N-hydroxysuccinimide (NHS) esters, sulfoNHS esters, epoxides, halogenated triazines, aldehydes, hydrazines, iodoacetamides, maleimides, and other cross-linking groups known in the art. In some embodiments a human arginase used in such processes can be genetically modified, for example in order to restrict or reduce the number and/or location of modifiable amino acid side chains present on the human arginase. For example, the number of reactive amines can be reduced by replacing one or more lysines in the sequence of a human arginase with another amino acid. Similarly, the number of reactive thiols can be reduced by replacing one or more cysteines in the sequence of a human arginase with another amino acid.

It should be appreciated that the addition of a polyhistidine sequence (for example, at the amino and/or carboxyl terminus), which is commonly used to produce a fusion protein with an affinity for nickel, is not necessary in composition or methods of the inventive concept. An example of a suitable recombinant arginase is provided in SEQ ID NO: 1. Inclusion of such a polyhistidine sequence can potentially render the human arginase antigenic, and therefore unsuitable for repeated use as a therapeutic agent. In addition, inclusion of a polyhistidine sequence would interfere with isolation of the arginase using cation exchange during initial purification and subsequent to modification reactions described above.

PEGylation is frequently used to extend serum half life of proteins having therapeutic value. Such processes are generally carried out using a large molar excess (e.g. 10-fold molar excess or greater) of a reactive form of PEG in order to make sure that a significant fraction of the subject protein is PEGylated. This is particularly in true in proteins that present with steric issues that reduce coupling efficiency, such as human arginase 1. Typical reactive forms of PEG include PEG-NHS or PEG-sulfoNHS (used when coupling through an amine is desired) or a PEG-maleimide (used when coupling though a thiol is desired). Use of a large molar excess of such activated PEG is undesirable for a number of reasons, including the possibility of coupling with reduced selectivity at large molar excess, subsequent difficulty in separating the large excess of unreacted PEG from the reacted protein, and expense.

Surprisingly, Inventors have found that human arginase (such as human arginase 1 purified as described above) can be efficiently PEGylated using a very low (e.g. 3-fold to 4-fold relative to protein content) molar excess of a PEG-maleimide. Even more surprising, this PEGylation can be performed at high efficiency under selective conditions (e.g. mildly acidic pH, which blocks potentially reactive amines by protonation) at low temperatures (both of which reduce reactivity) and extended (i.e. greater than 1 hour and/or up to 72 hours) reaction times. Inventors have found that such methods can provide PEGylation of essentially all (i.e. greater than 90%) of the human arginase 1 provided and that separation from the relatively small amount of unreacted or hydrolyzed PEG that remains can be readily accomplished by gel filtration and/or ion exchange. In some embodiments the human arginase thus modified can be genetically modified to provide a reduced number of potentially reactive cysteines relative to the native sequence. In a preferred embodiment the human arginase can be a modified human arginase 1 providing a single cysteine and that does not include a poly-histidine sequence. In some embodiments the human arginase can include a non-native (i.e. not manganese) metal cofactor, such as cobalt or nickel.

Examples

Cell Disruption, Extraction and Clarification

An *E. coli* clone (strain: BL21 Star™, Invitrogen) containing an ampicillin-resistant, transient and constitutive expression vector pET-3a was transformed with cDNA encoding for human arginase-1 and established in culture. A cell paste produced from such a culture with a wet weight of 42.2 g was washed with 230 mL lysis buffer (50 mM Tris pH 7.9, 1 mM $MgSO_4$) followed by centrifugation for collection of cell paste. After re-suspension of the cell paste with 210 mL lysis buffer and 35 mL was drawn for further processing.

Human arginase was released from 35 mL of the cell re-suspension by sonication using a Q700 Sonicator (Qsonica) and the following duty cycle: 10 seconds ON, 30 seconds OFF, ON for 3.5 minutes) to yield a homogenate. After centrifugation (10,000 rpm, 15 minutes), the resulting supernatant was collected and subjected to thermal precipitation (65° C. for 15 minutes) in the presence of $CoCl_2$ in a water bath. The precipitate was removed by centrifugation and the supernatant was subjected to additional purification steps. FIG. 2 shows SDS-PAGE results for the homogenate and the results of thermal precipitation in the presence of various amounts of $CoCl_2$, indicating that an optimal recovery of arginase was observed at a temperature of 65° C. for about 15 min in the presence of $CoCl_2$ of at least 20 mM. This step of process not only removed heat-sensitive impurities but also replaced chelating ions with cobalt.

Partial Purification by Anion Exchange Chromatography

The supernatant produced by thermal precipitation (26.5 mL) was filtered through a 0.45 µm filter (Agilent, Captiva™ Econofilter PES membrane, 25 mm, 0.45 µm) and diluted with 100 mL MilliQ™ water and 110 mL 20 mM Tris buffer pH 8.1 to yield a loading sample (pH 7.95, conductivity: 1.213 mS/cm).

Figure 3:
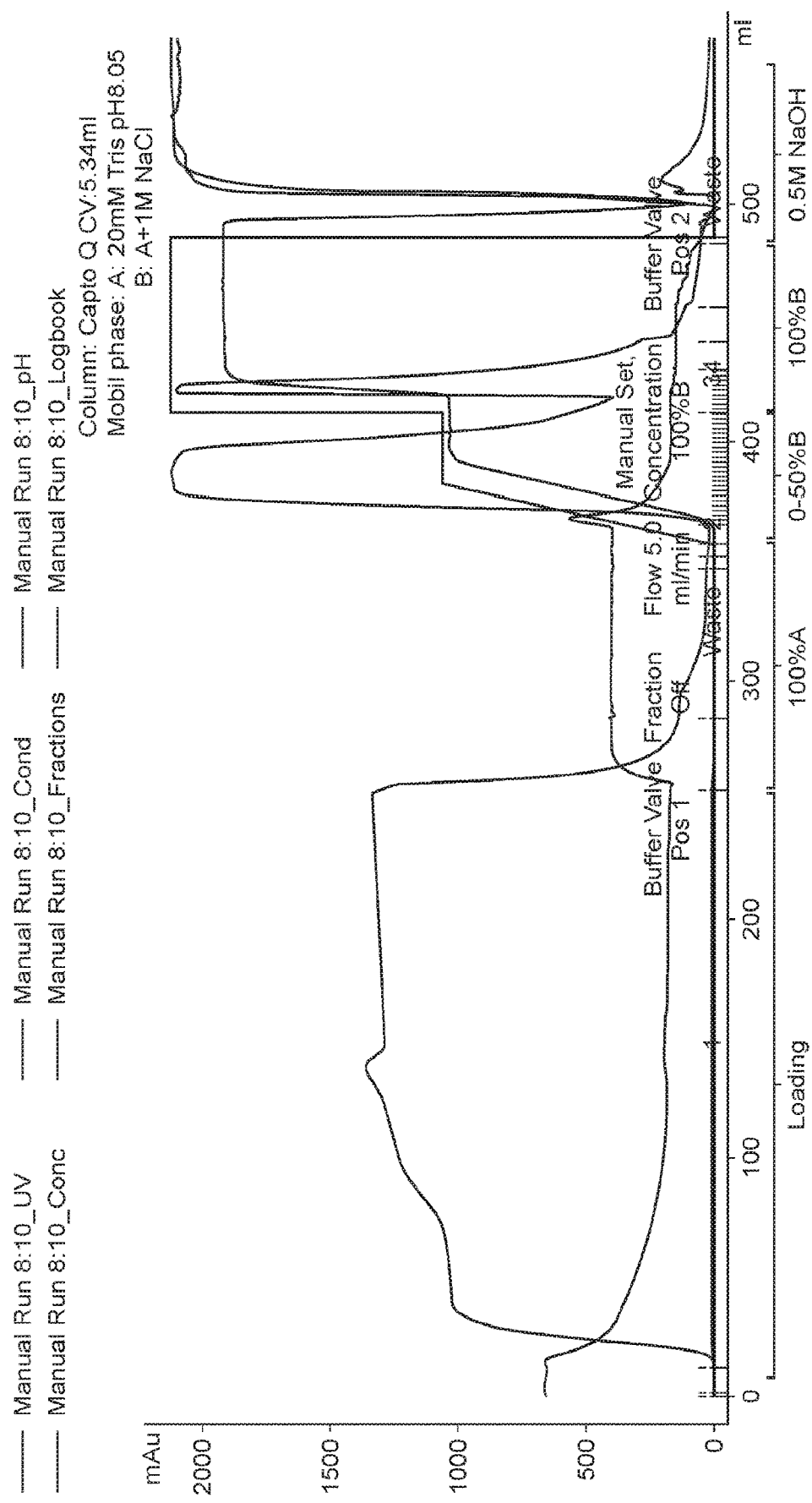
FIG. 3: A graph of UV absorbance during chromatography over Capto Q™.
Figure 4:
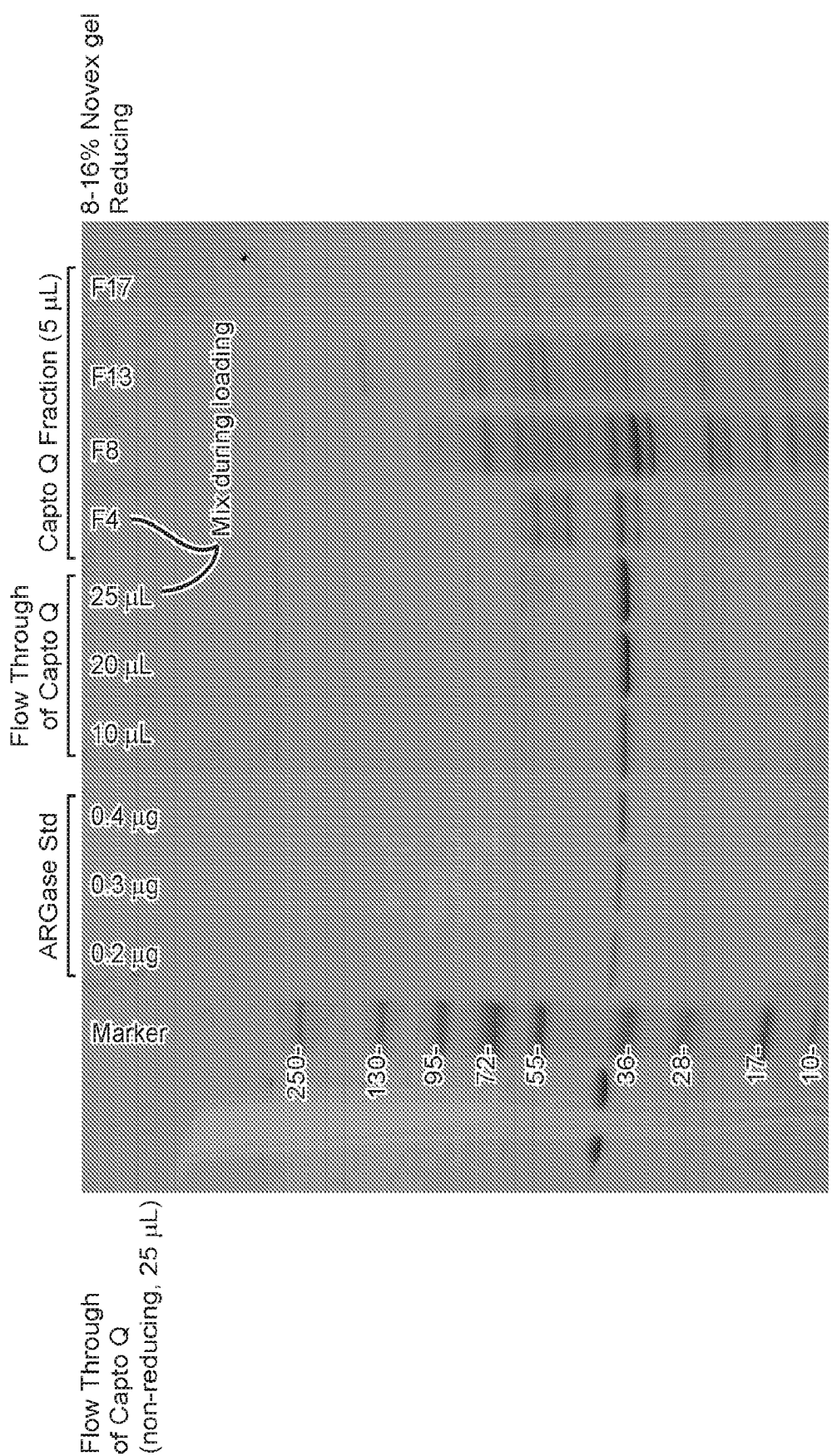
FIG. 4: A photograph of a electrophoresis gel showing results from reducing SDS-PAGE on an 8-16% gradient gel for a typical Capto Q™ chromatography step.

The purification was carried out by FPLC on an AKTA™ prime plus (GE Healthcare Life Sciences) fitted with a chromatography column packed with Capto Q™ (1×6.8 cm, GE Healthcare Life Sciences) that had been previously equilibrated with 20 mM Tris buffer pH 8.1. The flow through was collected at the flow rate of 3.5 mL/min for further purification. UV absorption was monitored during this process; the results are shown in FIG. 3. The results of SDS-PAGE analysis of fractions collected during Capto Q™ chromatography are shown in FIG. 4. It is apparent that human arginase 1 remains in the flow through fraction, along with some minor contaminants.

Figure 5:
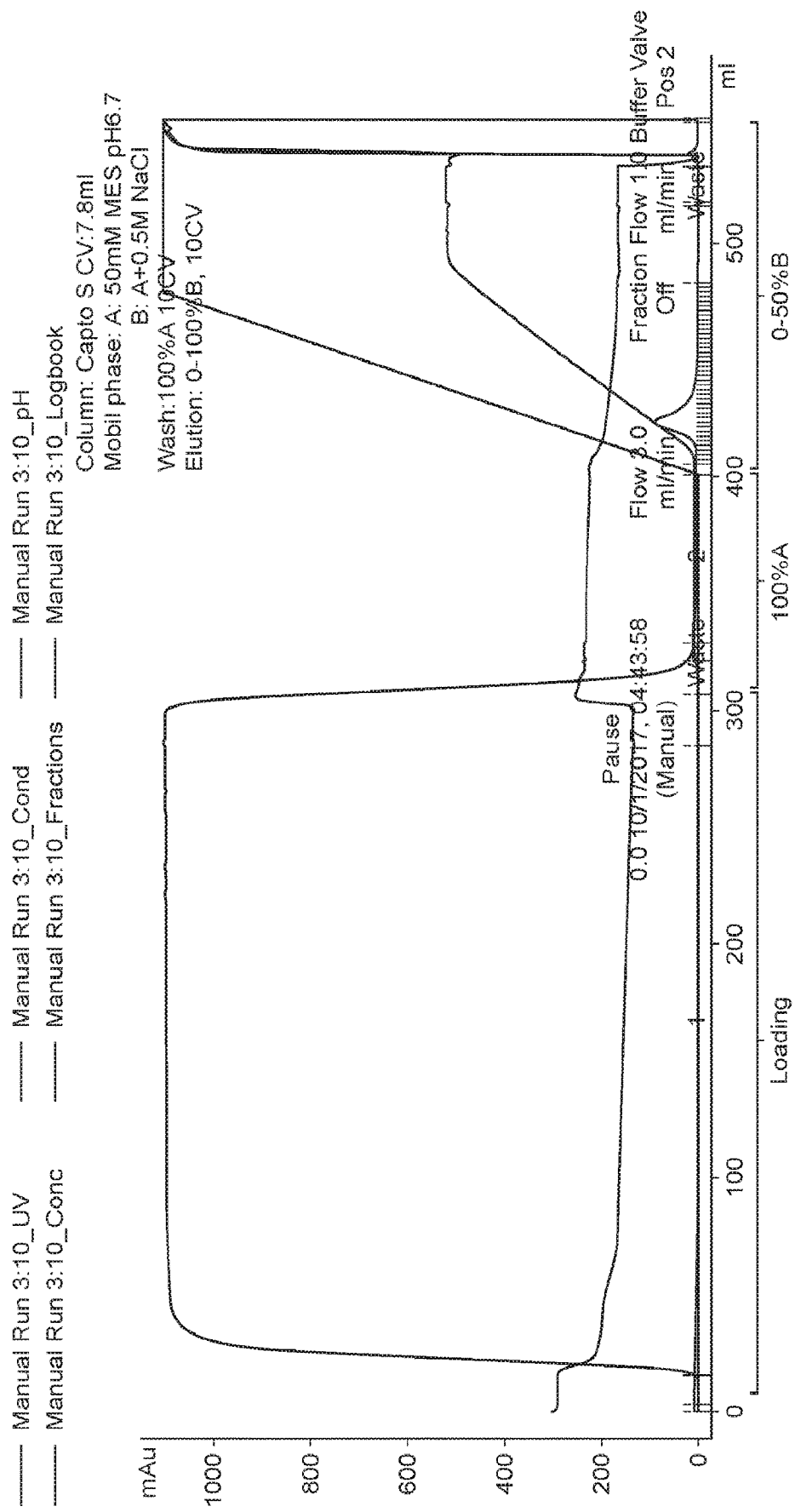
FIG. 5: A graph of UV absorbance during chromatography over Capto S™.
Figure 6:
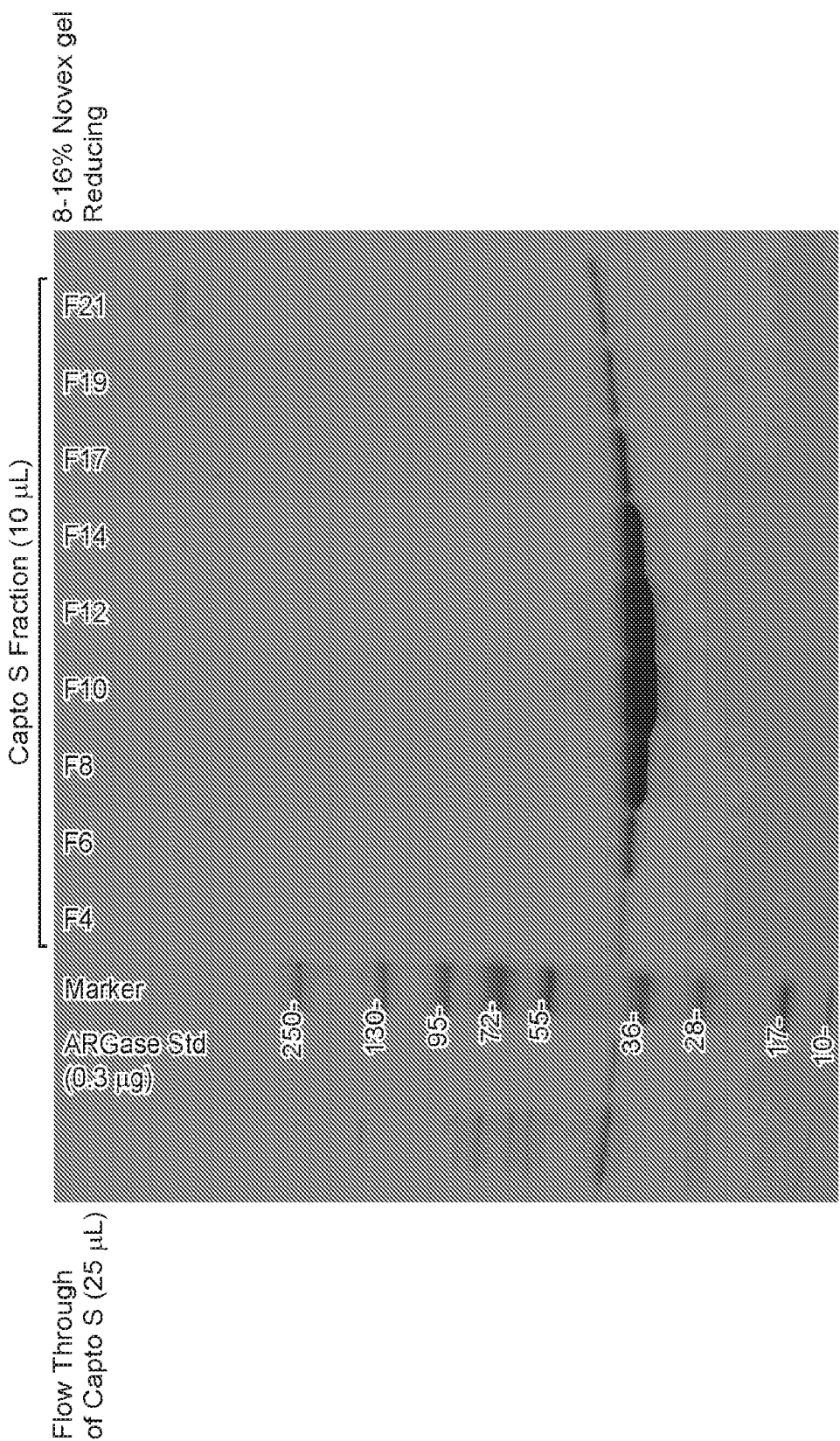
FIG. 6: A photograph of a electrophoresis gel showing results from reducing SDS-PAGE on an 8-16% gradient gel for a typical Capto Q™ chromatography step.

Additional Purification by Cation Exchange Chromatography 15 mL of 50 mM MES (MES monohydrate) buffer pH 6.7 was added to the flow through fraction obtained from the Capto Q™ column and the pH was adjusted to 6.2 by adding 6N hydrochloric acid before loading onto a Capto S™ column (1×10 cm, GE Healthcare Life Sciences) at a flow rate of 3.9 mL/min. The Capto S™ column was previously equilibrated with 50 mM MES buffer pH 6.7. Human arginase 1 was eluted with a linear gradient of 0 to 0.5 M NaCl in the equilibration buffer. UV absorbance was monitored; typical results are shown in FIG. 5. The results of SDS-PAGE analysis of fractions collected during Capto S™ chromatography are shown in FIG. 6. It is apparent that human arginase 1 is eluted at high purity using a simple NaCl gradient, with only very minor contaminants noted apparent the SDS-PAGE gel is overloaded.

The lack of contaminants apparent even at protein concentrations that overload the SDS-PAGE gel indicate a purity of at least 90%, 95%, 98%, 99%, or greater for this human arginase 1 preparation. It should be appreciated that this purity accomplished without the need for a poly-histidine or other affinity "tag" sequence, and represents purification of a native protein sequence. Inventors contemplate that methods and compositions of the inventive concept can be utilized to purify sequence modified and/or derivatized (for example, PEGylated) human arginase, and for separation of derivatized from unreacted human arginase in reaction products of the derivatization reactions.

Process Yield and Estimate of Expression Level

Table 1 provides estimates of process yields at various points in the purification process. Protein concentrations were measured by densitometry using Image Studio Lite™ Version 5.2 (LI-COR Biosciences), except that of pool of Capto S which is measured by UV absorbance at 280 nm using a UV spectrophotometer (Multiskan™ GO, Thermo Scientific™). The extinction coefficient at 280 nm is 0.703 for 1 mg/mL.

TABLE 1

|  | Conc. (mg/mL) | Vol. (mL) | Total Protein (mg) | Step Yield (%) |
| --- | --- | --- | --- | --- |
| Homogenate | 2.03 | 30.0 | 61.0 | N/A |
| -Supernatant | 0.88 | 30.0 | 26.3 | 43.1 |
| Thermal Precipitation | 1.49 | 26.5 | 39.4 | 150.0 |
| FT of Capto Q | 0.07 | 271.6 | 17.8 | 45.0 |
| Pool of Capto S (F6-21) | 0.54 | 32.0 | 17.4 | 97.9 |

Overall yield in this example was estimated at 28.5%.

Preparation of Conjugated Human Arginase 1 with Various PEG Moieties

Purified a sequence modified cobalt-chelated human arginase-1 (SEQ ID NO: 1) with a catalytic activity of 300-450 U/mg and purified as described above was obtained for subsequent PEGylation with different maleimide-derivatized PEGs. Four PEG-maleimides were employed for selective conjugation, namely 20 L (a 20-KD linear PEG-maleimide, purchased from Jenkem Technology USA, Cat #M-MAL-20K), 20V Sinopeg #06020101912 (a 20-KD "V" configured PEG-maleimide, purchased from NOF Corp., Cat #GL2-200MA), 20Y (a 20-KD "Y" configured PEG-maleimide, purchased from Sinopeg #06020501954), and 40Y (a 40-KD "Y" configured PEG-maleimide, purchased from Jenkem Technology USA, Cat #Y-MAL-40K). For conjugation, 5 mg/mL of the above human arginase 1 was reacted with different molar ratios of the respective PEG reagents at 4-10° C. at pH 6.7. The reaction mixture was incubated at this reduced temperature for at least 48 hours. The monopegylated product was then isolated with size-exclusion chromatography, or cation-exchange chromatography (which can be more suitable for large scale preparation). For cation exchange chromatography, a MacroCap™ SP column was used to purify PEGylated products using 20 mM MES pH 6.3 buffer containing 0.1M NaCl as the elution buffer.

Fractions containing monopegylated product, as determined by SDS-PAGE, were pooled, concentrated and dialyzed against PBS pH 7.4 buffer. The final protein concentration was directly determined by ultraviolet spectroscopy at 280 nm, using a extinction coefficient of 0.703 for a 0.1% (1 mg/ml) solution.

Maleimide-derivatized PEG is effective for protein conjugation of sulfhydryl groups to form a stable thioether bond, efficiently at pH 6.5 to 7.5. Reactivity towards primary amines can occur when pH is greater than 7.5, and the stability of the maleimide group decreases as the pH increases. Human arginase is known to be relatively resistant to conjugation using such derivatized hydrophilic polymers. Human arginase is a homotrimer; Inventors believe (without wishing to be bound by theory) that conjugation of the first PEG molecule is likely to hamper a second conjugation on the homotrimer even though the sulfhydryl conjugation reaction is selective (for example, by steric hindrance). As a result, a large excess molar ratio of PEG reagent is usually utilized to ensure a complete reaction. For example, under conventional reaction conditions a 6-fold molar addition of PEG yielded 71.1% monopegylated product after 35 hours of incubation at room temperature; and an 8-fold molar excess addition yielded 86.3% monopegylated product after 46 hours of incubation at room temperature.

Surprisingly, Inventors have found that high conjugation yields can be achieved using minimal PEG reagent when the conjugation reaction takes place at a reduced temperature (e.g. less than 10° C.), even when using stringent conjugation conditions (such as slightly acidic pH). Without wishing to be bound by theory, Inventors believe that reduced temperature prolongs the half-life of the maleimide coupling group, such that the probability of a 2nd and 3rd conjugation is increased. The pH for reaction can be about pH 6.7 in order to favor selective conjugation of sulfhydryl groups.

PEGylation kinetics were investigated with different molar ratios (e.g. 2-fold, 4-fold, 6-fold) of the PEG-maleimide reagent. Following addition of PEG-maleimide and incubation at about 4° C. the crude reaction mixture was diluted with a 4× volume of 20 mM MES pH 6.3 buffer prior to purification by a cation-exchanger (MacroCap™ SP). After loading the dilute reaction mixture onto the column, excess PEG was removed by washing with 20 mM MES pH 6.3 buffer. Monopegylated arginase was then eluted with the same buffer containing 0.1 M NaCl. The final product, after extensive dialysis against PBS buffer and concentration, had a specific activity of 425 U/mg.

Figure 7:
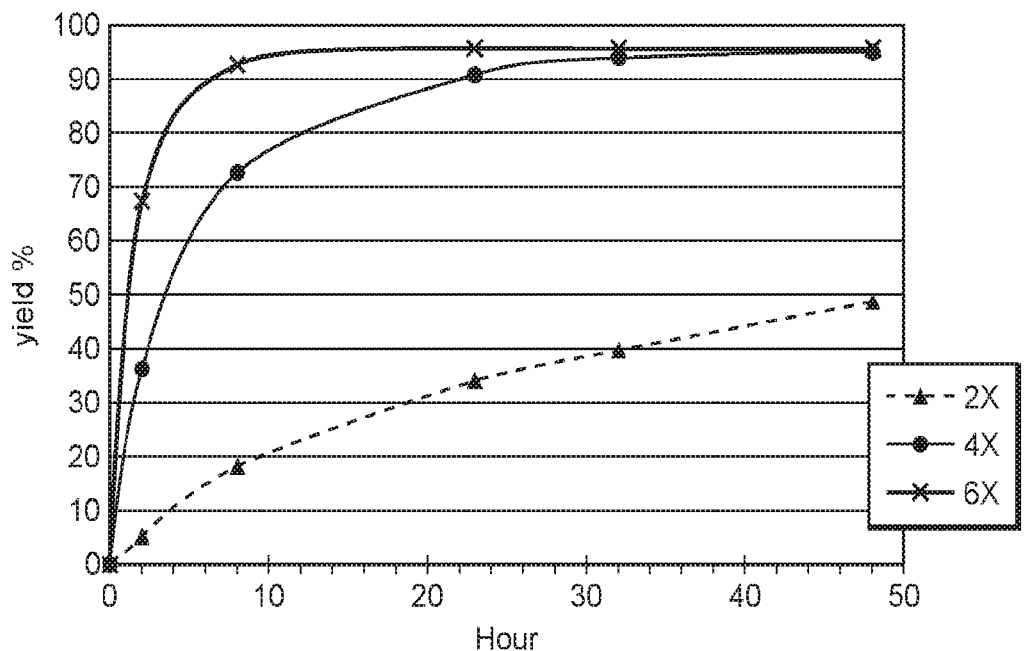
FIG. 7: A graph of PEGylation kinetics for human kinase 1 at 2-8° C. at different molar excesses of PEG-maleimide.

PEGylation yield (mono-PEGylated product) at reduced temperature over time was determined by reverse-phase ultra-performance liquid chromatography (RP-UPLC). Results are shown in FIG. 7, and indicate that a 4-fold molar excess of PEG-maleimide over human kinase 1 is sufficient to reached a 95% yield in 48 hours. Inventors believe that a 3-fold molar excess is sufficient to reach a similar yield given a prolonged incubation (e.g. 48 hours or more) at reduced temperature.

Pharmacodynamic Studies of PEGylated Human Arginase 1 in Healthy Rats

Animals: Three healthy juvenile male SD rats were selected for each test group. Rats of each group were administered a human arginase conjugate via IV delivery at the indicated dose. For each animal, a sample of about 0.8 mL of whole blood was collected from the jugular vein at appropriate time points using sample tubes containing an anticoagulant (Heparin Na) using 1-mL syringes. Plasma samples were prepared by immediate centrifugation of the blood sample at 3,000 rpm for 10 minutes. The supernatant (0.3-0.4 mL) was obtained and divided into 2 samples, and each was stored at −80° C.

Arginine quantitation: The plasma concentration of arginine was determined by comparison to known concentrations of arginine using an Agilent 6460 Liquid chromatography and Electrospray Ionization Triple Quadrupole MS system, using conditions as noted below and in Table 2.

Column: Agilent Zorbax RRHD HILIC Plus 95 Å, 2.1× 100 mm, 1.8 μm.
Mobile phase A: 5 mM NH$_4$COO—/0.1% formic acid; B: 0.1% formic acid in acetonitrile.
Flow rate: 0.2 ml/min; Injection vol. 1 μL.
Run time (including equilibration): 15 min.
Detection: Polarity +

| | Precursor ion | Product ion | Dwell | Fragmentor | Collision energy | Cell accelerator Voltage |
|---|---|---|---|---|---|---|
| Arginine | 175 | 70.3 | 270 | 130 | 22 | 4 |
| Synephrine | 168 | 150 | 200 | 50 | 2 | 4 |
| Ornithine | 135 | 72.1 | 270 | 130 | 28 | 4 |

Reference preparation: Prepare an arginine stock solution at 30 mM. Prepare working standards of arginine at 4, 10, 25, 75, 100, 150, 200, and 250 μM in 1% BSA/PBS buffer. Prepare the stock solution of synephrine at about 60 μg/mL. Synephrine is used as the internal standard to normalize recoveries of sample pretreatment procedures as described below.

Sample pretreatment: A plasma sample at 50 μL is added with 10 μL of the synephrine stock, followed by adding 540 μL MeOH to precipitate proteins in the sample. Vortex to ensure complete mixing. After centrifuge at top speed to spin-down precipitate, the supernatant is subjected to UPLC/MS analysis. Standards of arginine (4-200 μM) are also subjected to the same sample treatment procedures as above (add synephrine and MeOH precipitation).

Analysis and Calculation: Calculated areas of selected product ion in samples were used to determine the concentration of arginine against reference standards. The quantitation limit is about 5 μM.

Figure 8:
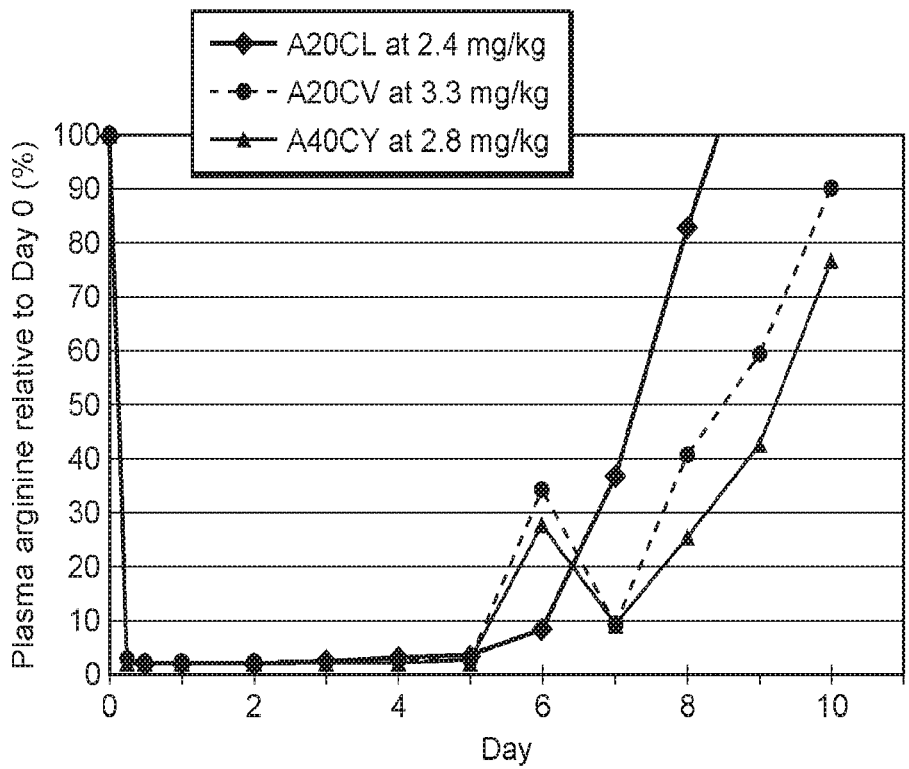
FIG. 8: A graph of plasma arginine concentrations in healthy rats following administration of a single intravenous dose of PEG-modified human arginase 1 on day 0.

The potential of arginine depletion was determined in healthy rats via a single intravenous (IV) delivery. Three conjugates, namely A20CL (arginine conjugated with 20 kD linear PEG), A20CV (arginine conjugated with 20 kD "V" branched PEG) and A40CY (arginine conjugated with 40 kD "Y" branched PEG) were given at 2.4 mg/Kg, 3.3 mg/Kg and 2.8 mg/Kg respectively due to miscalculation. Plasma arginine post-treatment was shown in FIG. 8, indicating successful arginine depletion 95% plasma arginine (relative to pre-dosing level) for about 5 days in healthy male rats.

Figure 9:
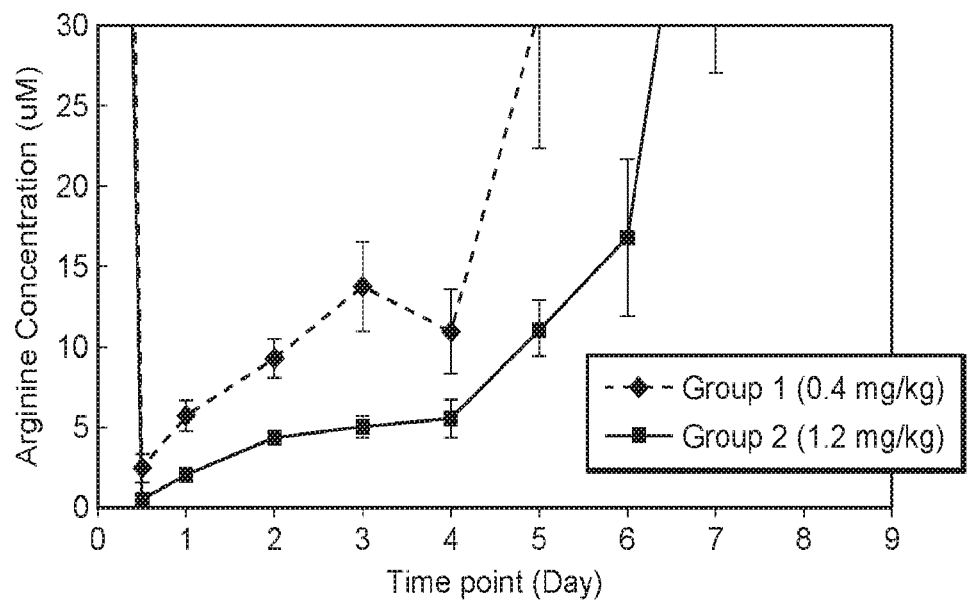
FIG. 9: A graph of plasma arginine concentrations in healthy rats treated with a single intravenous dose of PEG-modified human arginase 1 on day 0.
Figure 10:
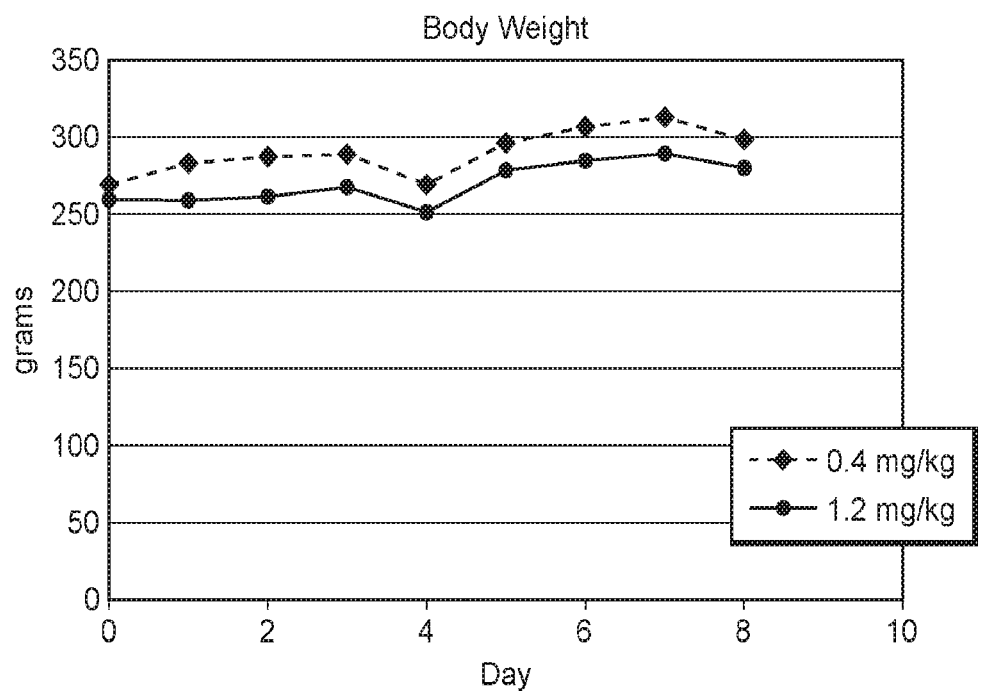
FIG. 10: A graph of body weight of healthy rats treated with a single intravenous dose of PEG-modified human arginase 1 on day 0.

A dose-finding study was carried out with rats receiving A20CL at 1.2 and 0.4 mg/kg through intravenous delivery, followed by monitoring of plasma arginine concentrations. Results are shown in FIG. 9. Treatment with A20CL at 1.2 mg/mL resulted in a low level of plasma arginine (<10 μM) for about 5 days. As shown in FIG. 10, no significant body weight loss was noted during treatment. This suggests that PEG-modified arginase is well tolerated.

Figure 11:
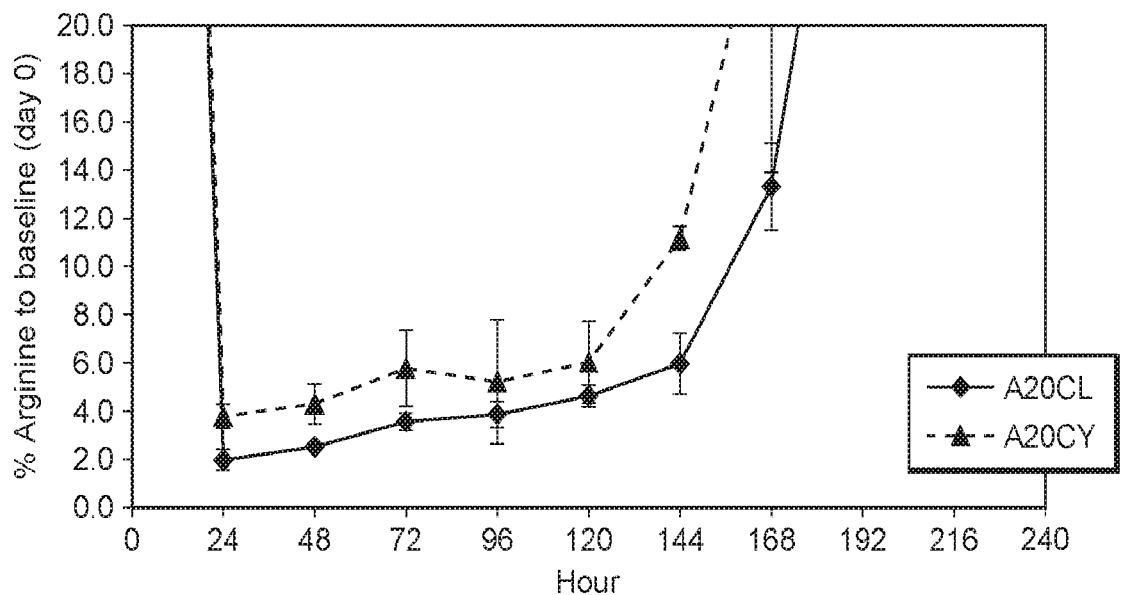
FIG. 11: A graph of plasma arginine concentrations in healthy rats treated with a single intravenous dose of linear and branched PEG-modified human arginase 1 on day 0.

Linear and branched PEGs were compared head-to-head with regard to their potential in modifying human arginase 1 for arginine depletion. Three male healthy rats were dosed with A20CL and A20CY respectively at 2 mg/kg on Day 0. The results of relative plasma arginine concentrations are shown in FIG. 11. As shown, both linear- and Y-form conjugates successfully deplete 90% of plasma arginine continuously for at least 5 days.

Figure 12:
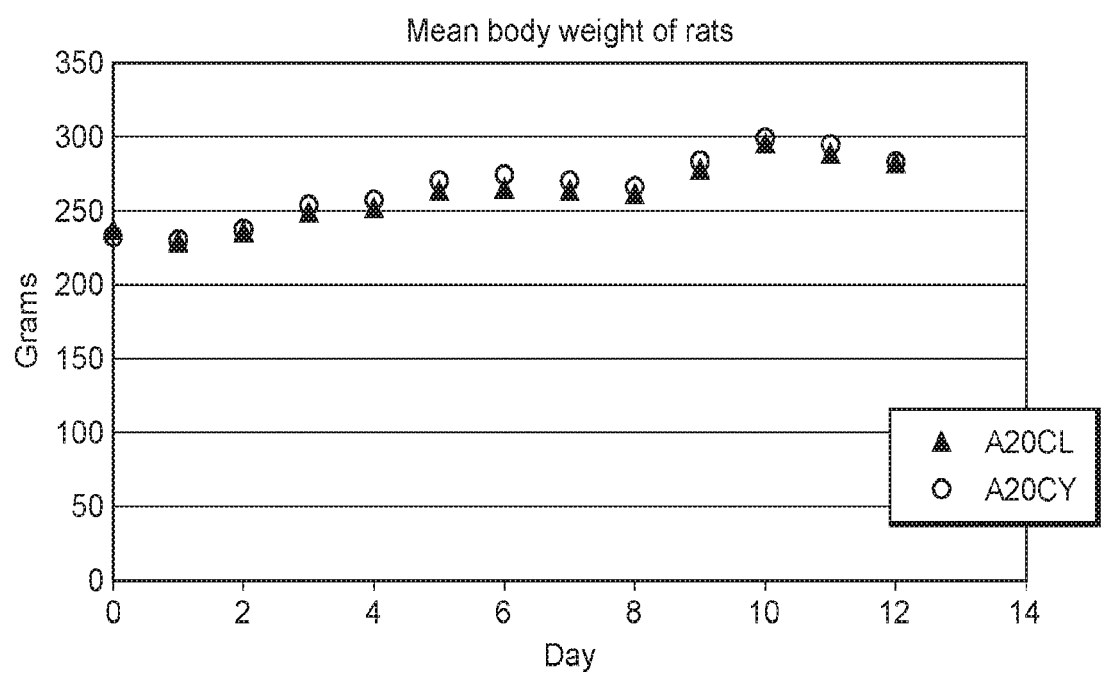
FIG. 12: A graph of body weight of healthy rats treated with a single intravenous dose of linear or branched PEG-modified human arginase 1 on day 0.

As shown in FIG. 12, no significant body weight loss was noted during treatment with linear or branched PEG-modified arginase. This suggests that both linear and branched PEG-modified arginases are well tolerated.

Molecular Mass of Human Arginase 1

The molecular mass of the mutant human arginase 1 was analyzed by reverse-phase (RP) chromatography employing a UPLC system coupled with an Agilent 6540 UHD Accurate Mass Q-TOF LC/MS system.

Figure 13:
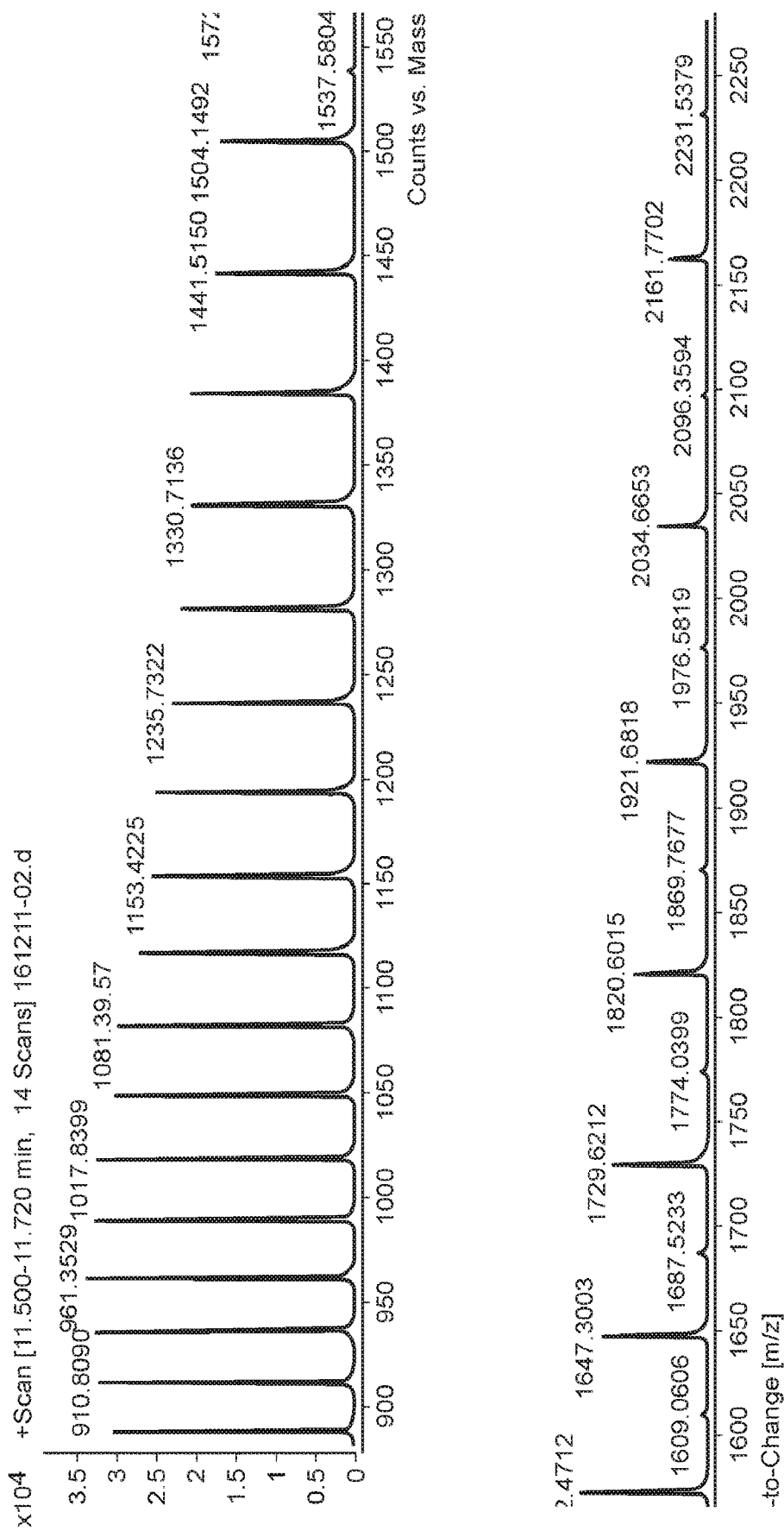
FIG. 13: Molecular mass determination by LC/Q-TOF MS. The deconvoluted mass of PEGylated arginase is 34,572.3 Da.

The mass spectrum m/z of the purified arginase is shown in FIG. 13, which indicates a deconvoluted mass of 34,572.3 Da. This is in good agreement with the averaged mass of 34,571.6 Da derived from the amino acid sequence of the mutant human kinase (i.e. without the N-terminal Met).

Peptide Mapping and Determination of Conjugation Site

A proteolytic solution was prepared in 50 mM Tris pH 8 buffer containing 2 mg/mL protein, and 2% (w/w) Lys-C of sequencing grade, in the presence of 4 M urea. After incubation at room temperature for 6 hr either TFA or formic acid was added to obtain a final concentration of 0.1% in order to quench the reaction. Precipitate was removed either by centrifugation or by filtration through a 0.2 or 0.4 μm membrane prior to injecting.

Peptide identification was carried out using an LC/MS system, specifically an Agilent 1290 infinity UPLC system coupled with an Agilent 6540 UHD Accurate Mass Q-TOF LC/MS system.

The chromatographic procedure was performed using conditions as listed below and in Table 3:

Column: same as utilized for molecular mass determination (see above)
Mobile phases and gradient:
 Mobile phase A: 0.1% (v/v) TFA in water
 Mobile phase B: 0.1% (v/v) TFA in 100% (v/v) acetonitrile
Flow rate: 0.4 mL/min
Injection: 10 μg

TABLE 3

| Time (min) | A % | B % |
|---|---|---|
| 0 | 100 | 0 |
| 2 | 100 | 0 |
| 30 | 55 | 45 |
| 30.01 | 10 | 90 |
| 35 | 10 | 90 |
| 35.01 | 100 | 0 |
| 45 | 100 | 0 |

Figure 14:
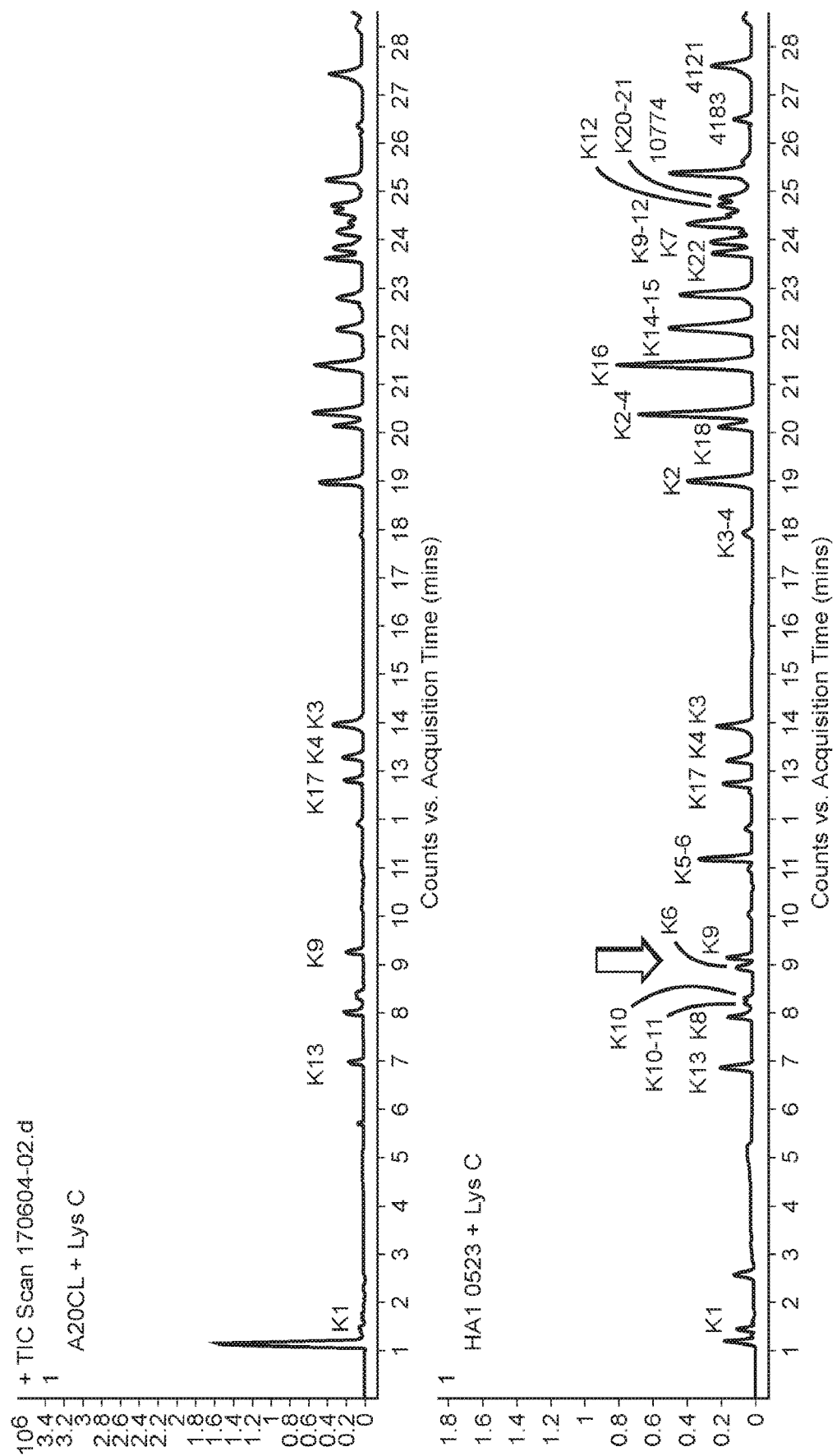
FIG. 14: Peptide map of mutant human arginase 1.

The PEGylation site of PEGylated human kinase 1 was identified by peptide mapping coupled with LC-MS. Protein was digested by endoproteinase Lys-C, which selectively hydrolyzes peptide bond on the C-terminal side of lysine residues in the presence of 4 M urea. All proteolytic peptides were successfully assigned as shown in FIG. 14, with lysyl peptides summarized in Table 4. The peptide map of the PEGylated human arginase 1 indicates conjugation at K6 peptide, where Cys-44 is the only site susceptible to sulfhydryl modification.

TABLE 4

| $MH^+$ | position | No. | peptide sequence |
|---|---|---|---|
| 305.2 | 1-3 | K1 | SAK |
| 1346.8 | 4-16 | K2 | SRTIGIIGAPFSK |
| 1679.9 | 17-32 | K3 | GQPRGGVEEGPTVLRK |
| 630.4 | 33-38 | K4 | AGLLEK |
| 260.2 | 39-40 | K5 | LK |
| 850.4 | 41-47 | K6 | EQECDVK |
| 2251.1 | 48-67 | K7 | DYGDLPFADIPNDSPFQIVK |
| 757.4 | 68-74 | K8 | NPRSVGK |
| 803.4 | 75-82 | K9 | ASEQLAGK |
| 545.3 | 83-87 | K10 | VAEVK |
| 147.1 | 88-88 | K11 | K |
| 6361.4 | 89-149 | K12 | NGRISLVLGGDHSLAIGSISGHARVHPDLGVIWVDAHTDINTPLTTTSGNLHGQPVSFLLK |
| 389.2 | 150-152 | K13 | ELK |
| 204.1 | 153-154 | K14 | GK |
| 1801.0 | 155-171 | K15 | IPDVPGFSWVTPSISAK |
| 2215.2 | 172-190 | K16 | DIVYIGLRDVDPGEHYILK |
| 531.4 | 191-195 | K17 | TLGIK |
| 1615.9 | 196-209 | K18 | YFSMTEVDRLGIGK |
| 1538.8 | 210-222 | K19 | VMEETLSYLLGRK |
| 147.1 | 223-223 | K20 | K |
| 4624.4 | 224-265 | K21 | RPIHLSFDVDGLDPSFTPATGTPVVGGLTYREGLYITEEIYK |
| 1844.0 | 266-283 | K22 | TGLLSGLDIMEVNPSLGK |
| 3082.6 | 284-312 | K23 | TPEEVTRTVNTAVAITLASFGLAREGNHK |
| 1056.6 | 313-321 | K24 | PIDYLNPPK |

Enzymatic Activity and Kinetics

Catalytic activity was determined by detecting diacetylmonoxine (DAMO) derivatization of urea in the presence of strong acids, thiosemicarbazide, and $Fe^{3+}$ with heating to produce a chromophore with a maximal absorbance at 540 nm. The assay was shown to be linear between 0 and 15 mM urea with a lower detection limit of 1.25 mM. Typically, reactions were initiated by warming 30 μL plasma samples and positive controls on a heat block pre-set to 37° C. for 3 minutes. After adding 30 μL arginine substrate, the mixture was incubated at 37° C. for exactly 5 minutes, followed by quenching by addition of 30 μL 25% trichloroacetic acid (TCA). After centrifugation, 10 μL working urea standards, samples/positive controls or blank controls were mixed with 300 μL of the color development reagent (containing DAMO and thiosemicarbazide) and the mixture was incubated on a heat block pre-set to 100° C. for exactly 10 minutes. The absorbance of the resulting sample at 540 nm was measured to determine urea concentration. The unit of arginase activity is defined as one mole of urea production per minute.

Figure 15:
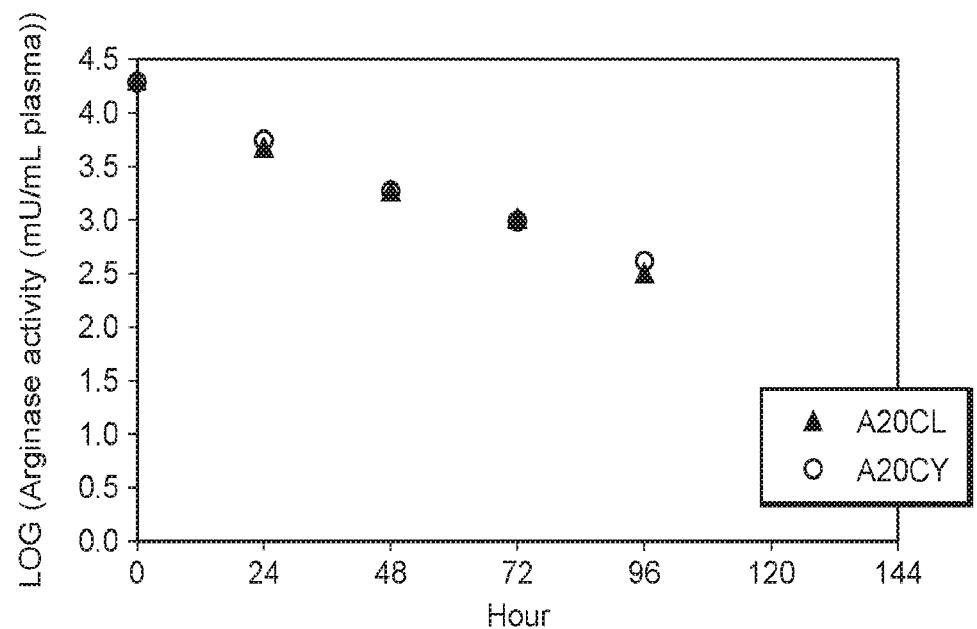
FIG. 15: A graph of enzymatic activity of arginase in rat plasma over time following a single intravenous dose of 2 mg/kg.

Arginase activity in plasma over time is shown in FIG. 15. The calculated half-lives (t½) of A20CL and A20CY were 17.0 hours and 17.6 hours respectively. Activity was not detectable in plasma samples taken after Day 5.

Enzyme-Linked Immunosorbent Assay (ELISA)

Plasma concentration of PEGylated human arginase 1 was determined using a sandwich ELISA. The assay utilized rabbit polyclonal antibody directed to human arginase 1

(Sino Biologicals #11558-RP01) as the capture antibody, and sheep polyclonal anti-arginase antibody (R&D systems #AF5868) with HRP-linked anti-goat-IgG antibody (R&D systems #HAF017) as detection antibodies.

Figure 16:
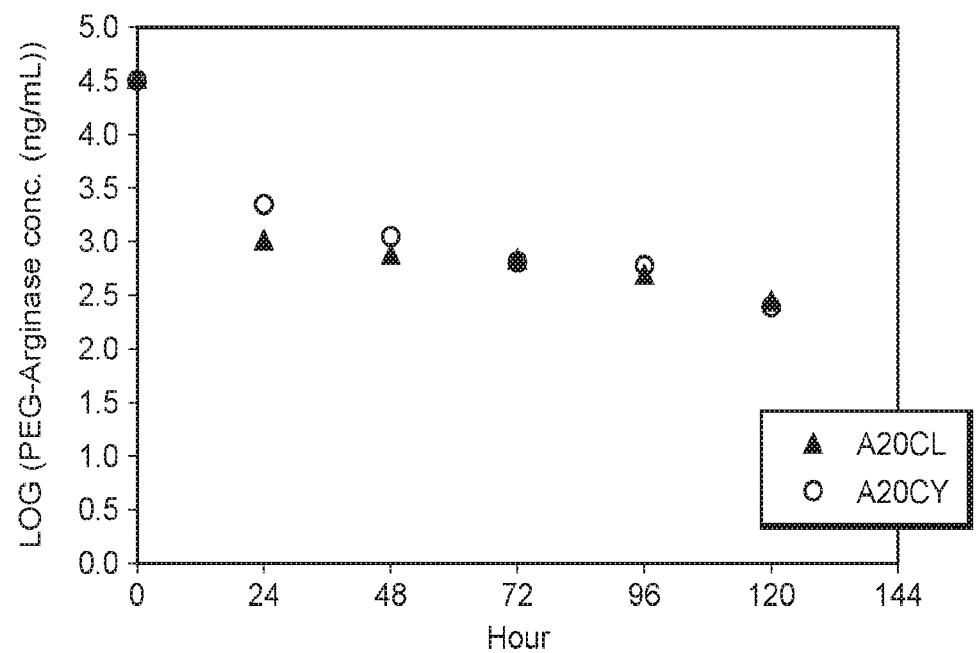
FIG. 16: A graph of plasma concentration of immunoreactive PEG-modified human arginase 1 in rat plasma over time following a single intravenous dose of 2 mg/kg.

Results of ELISA studies of plasma concentrations of immunoreactive PEG-modified human arginase 1 following a single IV dose of PEG-modified human arginase 1 at 2 mg/kg are shown in FIG. 16. The plasma concentrations of A20CL (conjugated with 20 L PEG) and A20CY (conjugated with 20Y PEG) were 1013±119 ng/mL and 2239±257 ng/mL respectively at 24-hour post-dose. Concentrations of all samples collected pre-dose and 120 hours post-dose were below the detection limit (160 ng/mL). Half-life was thus calculated at 22.6 hours and 20.3 hours for A20CL and A20CY respectively, which is consistent with the half life for enzyme activity noted.

In order to enhance the inhibitory effects of sequence-modified recombinant human arginase (rhArg), Inventors have deprived cancer cells of arginine and asparagine simultaneously using rhArg and asparaginase (ASNase). Inventors believe that asparagine deprivation can have at least a complementary effect to that of arginine deprivation due to asparagine's role as an amino acid exchange factor. It is thought that asparagine can regulated arginine import into the cell and thus influenced arginine mediated-mTORC1 activation. Inventors theorize that deprivation of asparagine can impair arginine transportation toward mTORC1 intracellularly.

The impact of deprivation of asparagine in cancer cell can depend on the amount of the asparagine producing enzyme asparagine synthetase (ASNS) present in the cell (Richards and Kilberg 2006; Balasubramanian, Butterworth et al. 2013; Liu, Dong et al. 2013). To evaluate the impact this may have Inventors utilized rhArg and ASNase to treat (i) the relatively low ASNS expressing breast cell lines MDA-MB-231, MCF7 and ZR-75-1 (Yang, He et al. 2014) and (ii) the high ASNS expressing cell lines HeLa (Guerrini, Gong et al. 1993), MIA-Paca-2 (Liu, Dong et al. 2013) and HepG2 (Gjymishka, Su et al. 2009). The efficacy of each drug individually (rhArg, ASNase) and combination were compared.

Examples

Exemplary procedures for the expression, purification, and PEGylation of recombinant human arginase (rhArg) are detailed above. One unit of arginase is defined as the amount of enzyme that produces 1 µmol urea per min at 30° C., pH 8.5. Asparaginase (ASNase) was purchased from Sigma (A3809).

MTT assay: Low ASNS expressing breast cancer cell lines (MCF-7, ZR-75-1 and MDA-MB-231) and high ASNS expressing cancer cell lines (HeLa, HepG2 and MIA-Paca-2) were purchased from ATCC. Cells were seeded in 96-well plate at densities of $5 \times 10^3$ cells/well. After 1 day of incubation, the culture medium was replaced with medium containing various concentrations of rhArg. For the combination assay (i.e. utilizing both arginase and asparaginase), the culture medium was replaced with medium containing different concentrations of rhArg and ASNase in a constant molar ratio (e.g. 5 rhArg: 1 ASNase) (Chou 2010). The MTT assay was conducted at Day 3 (3 days after drug treatment). The culture medium was replaced with MTT solution (1 mg/ml) (Invitrogen) and incubated at 37° C. for four hours. After four hours of incubation, MTT solution was replaced with dimethyl sulfoxide (DMSO), and the absorbance at 570 nm was measured with a reference of 650 nm. Cell viability was determined by dividing the absorbance of treated cells by the average absorbance of untreated cells. Three independent sets of experiments (n=3) were performed for each cell line. The data were analyzed using Prism™ version 6.01.

Combination index (CI) calculation: The combination index of rhArg and ASNase treatment was calculated using CalcuSyn™ version 2.1. CI provides a value for the combination effects of the drugs, such as greater than additive (CI<1, synergistic), less than additive (CI>1, antagonistic), or similar to additive (CI=1) effects.

Figure 17:
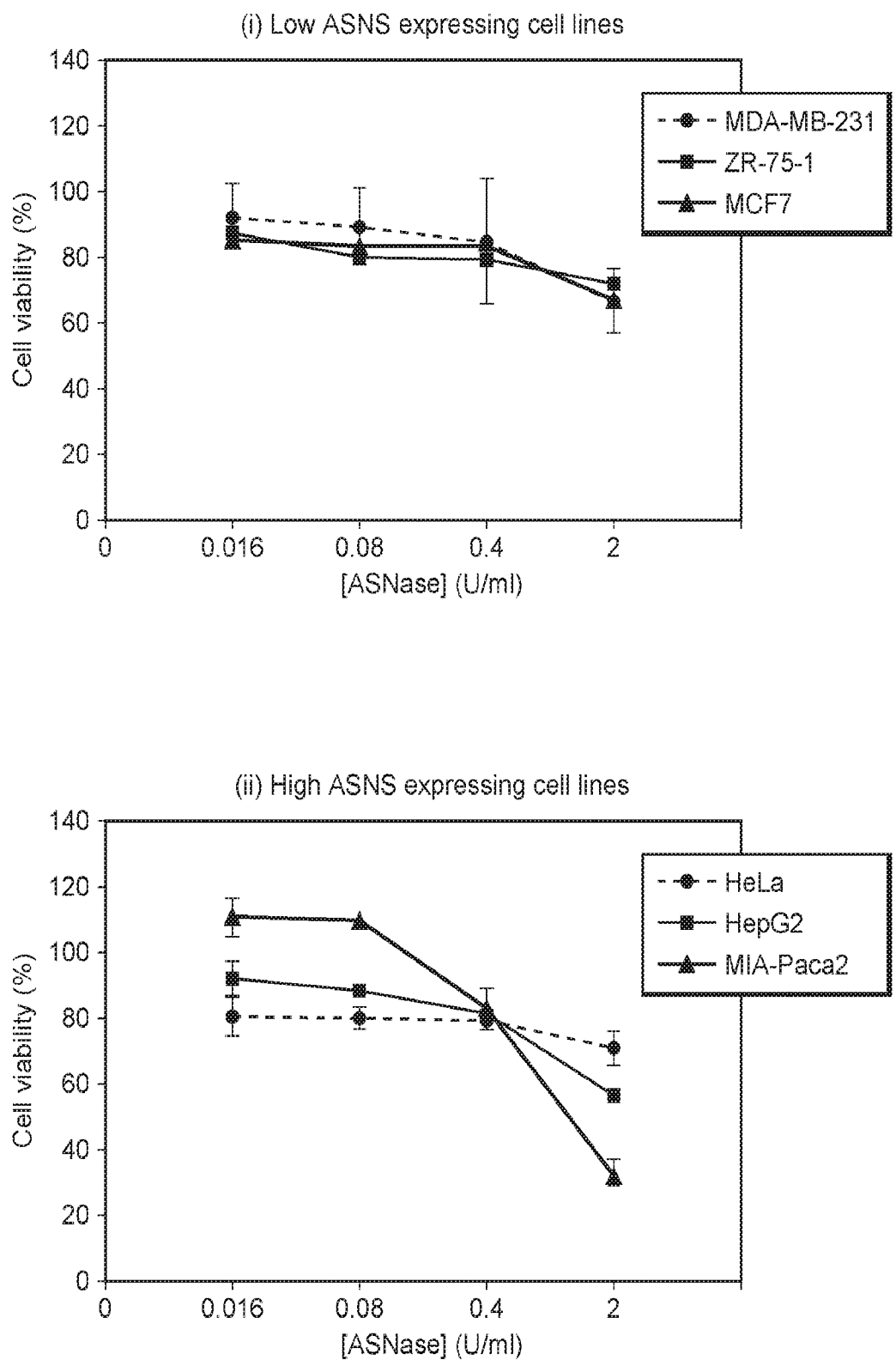
FIG. 17: Graphs of the efficacy of ASNase alone in (i) low ASNS expressing cell lines (MDA-MB-231, ZR-75-1 and MCF7) and (ii) high ASNS expressing cell lines (HeLa, HepG2 and MIA-Paca2). Three sets of independent trials were performed for each experiment. Error bars represent one standard deviation (SD).

Inventors found that ASNase alone did not provide satisfactory inhibitory effects for most of the low and high ASNS expressing cell lines. The dose-response curves of ASNase in (i) low ASNS expressing and (ii) high ASNS expressing cancer cells are shown in FIG. 17. ASNase exhibited a low inhibitory effect (<20% cell inhibition) ranged from 0.016 to 0.4 U/ml. 60-70% cell viabilities can be detected at MDA-MB-231, ZR-75-1, MCF7, HeLa and HepG2. About 40% cell viability was detected at MIA-Paca-2.

Figure 18:
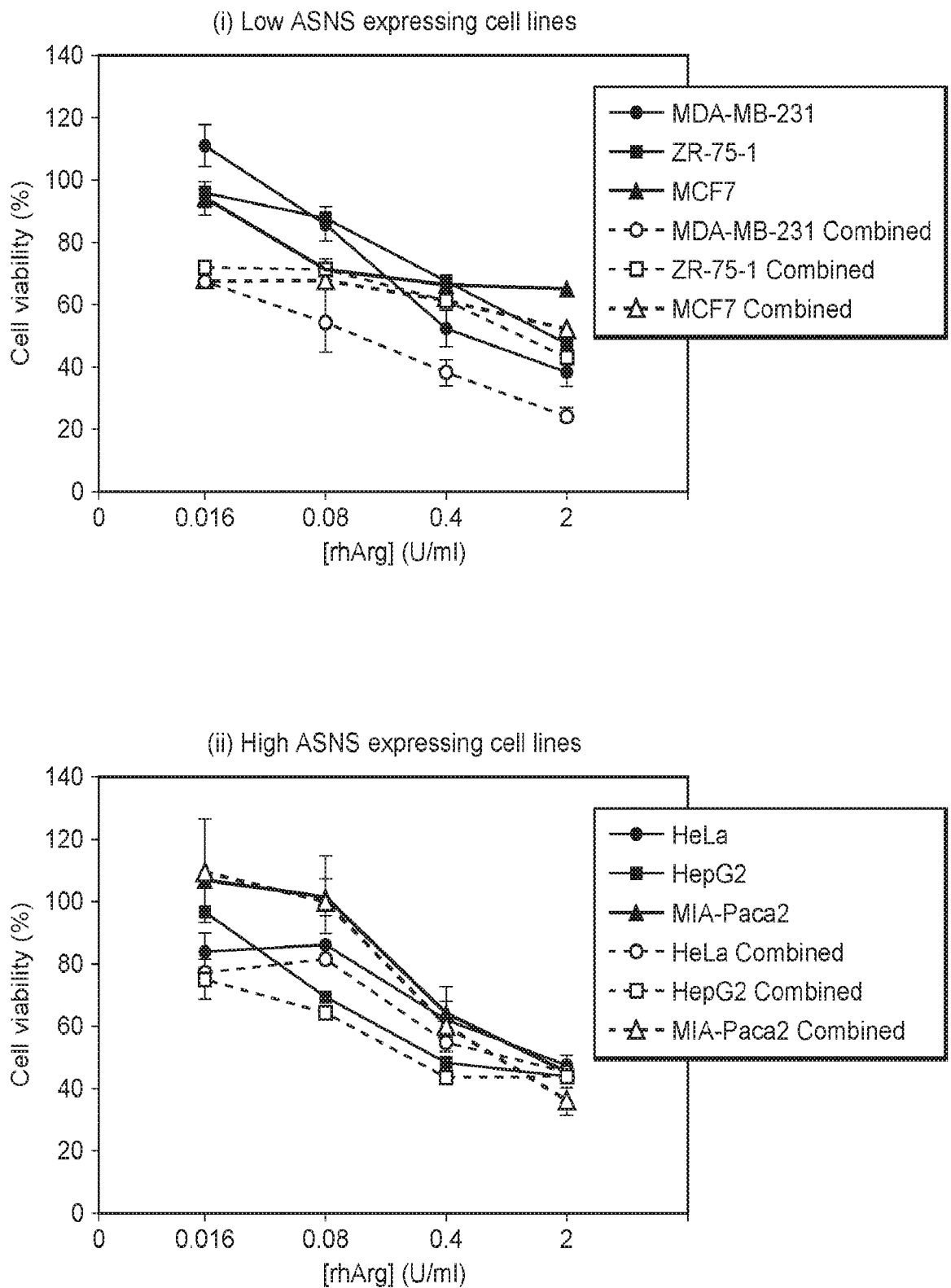
FIG. 18: Graphs of the efficacies of rhArg alone and rhArg-ASNase-combination in (i) low ASNS expressing cell lines (MDA-MB-231, ZR-75-1 and MCF7) and (ii) high ASNS expressing cell lines (HeLa, HepG2 and MIA-Paca2). Three sets of independent trials were performed for each experiment. Error bars represent one standard deviation (SD).

Surprisingly, a combination of rhArg and ASNase provides substantially improved inhibitory effects compared with rhArg alone in low ASNS expressing cell lines. The dose-response curves of rhArg alone (solid line) and combination of rhArg and ASNase (dashed line) in (i) low ASNS expressing and (ii) high ASNS expressing cancer cells, as shown as FIG. 18. In low ASNS expressing cell lines, combined rhArg and ASNase treatment provided a dramatically improved cell inhibitory effect at various concentrations. Combined rhArg-ASNase treatment showed satisfactory improvement on inhibitory effect in MDA-MB-231. In high ASNS expressing cell lines, combined treatment on average slightly improved (<5%) inhibitory effects. Inventors found that rhArg-ASNase combination therapy provided unexpected strong synergistic effects in low ASNS expressing cell lines but not in high ASNS expressing cell lines.

Combination indices (CI) of rhArg and ASNase combinations with different concentrations are shown in Table 5. Surprisingly, for low ASNS expressing cell lines MDA-MB-231, ZR-75-1 and MCF7 all of the combinations exhibited synergistic effects on inhibiting the cancer cell growth (CI<1). For high ASNS expressing cell lines HeLa, HepG2 and MIA-Paca2, most of the rhArg and ASNase combinations showed antagonistic effects on inhibiting the cell growth (CI>1).

TABLE 5

| Low ASNS Expressing Cell Lines | | | |
|---|---|---|---|
| Combinations 5 rhArg:1 ASNase (U/mL) | MDA-MB-231 | ZR-75-1 | MCF7 |
| 0.016:0.0032 | 0.040 | 0.044 | 0.022 |
| 0.08:0.0016 | 0.129 | 0.204 | 0.726 |
| 0.4:0.08 | 0.435 | 0.506 | 0.777 |
| 2:0.4 | 0.964 | 0.827 | 0.272 |
| High ASNS Expressing Cell Lines | | | |
| Combinations 5 rhArg:1 ASNase (U/mL) | HeLa | HepG2 | MIA-PAca2 |
| 0.016:0.0032 | 1.166 | 0.109 | 1.139 |
| 0.08:0.0016 | 2.576 | 1.044 | 3.794 |

TABLE 5-continued

Low ASNS Expressing Cell Lines

| 0.4:0.08 | 1.014 | 1.269 | 1.015 |
| 2:0.4 | 1.112 | 2.064 | 1.351 |

Inventors have found that the deprivation of asparagine alone provides little inhibitory effect on cancer cells. Such asparagine deprivation alone does not appear to be an effective method for treating cancers, with the exception of acute lymphoblastic leukemia (ALL). Inventors theorize that the effectiveness of ASNase on ALL by the low expression of asparagine synthetase (ASNS) in these leukemic cells (Su, Pan et al. 2008).

Inventors theorize that in combined therapy as described above arginine deprivation can provide deactivation of mTORC1, while asparagine deprivation can impair arginine import to mTORC1 protein intracellularly. The efficacies of the combined therapy can be impacted by the ASNS expression level of the cancer cell, as high ASNS expression levels can generate asparagine from glutamine (Horowitz and Meister 1972). HeLa, HepG2 and MIA-Paca2, which exhibit high ASNS expression levels, showed reduced improvement on combination therapy relative to cancer cells exhibiting low ASNS levels. CI calculation show that low ASNS expressing cell lines such as MDA-MB-231, ZR-75-1 and MCF7 exhibit pronounced rhArg-ASNase synergistic effects at most combined concentrations. However, poor synergistic effects are observed in high ASNS expressing cell lines such as HeLa, HepG2 and MIA-Paca2. The results were consistent with cell viability assays. Inventors theorize that high ASNS expressing cell lines are capable of generate sufficient asparagine to mitigate the efficacy of the combination therapy. Inventors believe that the expression level of ASNS can be used to predict the effectiveness of rhArg-ASNase combination therapy and can be useful for developing tailor-made drug therapies.

Based on the results of combination therapy with arginase and asparaginase on various cancer cell lines, Inventors believe that glutamine can also be deprived simultaneously with arginine and asparagine in vitro for cancer treatment. The efficacy of glutamine-depriving therapy greatly depends on the expression level of c-MYC expression (Wise and Thompson 2010). Inventors believe that combination therapy with compounds to reduce arginine (such as arginase), asparagine (such as asparaginase) and glutamine (such as the aminotransferase inhibitor aminooxyacetate or AOA, 6-diazo-5-oxo-L-norleucine, azaserine, and/or acivicin) can be highly effective at inhibiting the growth of cancer cells. Without wishing to be bound by theory, Inventors hypothesize that arginine, asparagine, and glutamine deprivation can deactivate mTORC1 by arginine removal (e.g. by rhArg), and the intracellular arginine concentration can be maintained at low level by a reduction in asparagine and glutamine (e.g. by ASNase and AOA).

Arginase can be PEGylated at high efficiency and isolated at high purity, specific activity, and yield using the above described methods. Such PEGylated arginase exhibits an extended half life in vitro, is effective in reducing arginine concentration, and is well tolerated. As such Inventors believe that arginase isolated and conjugated as described above is particularly well suited for therapeutic use in the treatment of cancer, particularly when such cancer shows low asparaginase activity. Based on evidence of unexpected and significant synergistic effects against different cancer cell lines when used in combination with asparaginase, Inventors believe that a PEGylated arginase prepared as described above and used in combination with asparaginase can provide similar synergistic effects in the treatment of cancer. Asparaginase utilized in such treatment methods can also be PEGylated or conjugated with similar hydrophilic polymers in order to extend serum half life.

In a preferred embodiment, arginase and asparaginase are provided that present similar pharmacokinetics, thereby permitting simultaneous administration. Such enzymes can be provided by any suitable method, including injection, infusion, and/or adsorption across a mucous membrane (for example, by inhalation). Suitable treatment schedules can be determined by the pharmacokinetics of the enzymes utilized, and can be adapted to accommodate different tumor types and/or phenotypes. For example, an individual with a tumor expressing relatively high levels of asparaginase can be treated more frequently and/or with higher doses of arginase and/or asparaginase than an individual with a tumor expressing lower levels of asparaginase. Suitable treatment protocols can include administration of arginase, asparaginase, and/or a mixture of arginase and asparaginase every 12 hours, 24 hours, 36 hours, 48 hours, 3 days, 4 days, 5 days, 7 days, 10 days, 14 days, 21 days, 28 days, or more than 28 days. In some embodiments the frequency of administration can vary throughout the course of treatment, and can include a maintenance dosing that extends beyond the period of initial treatment. In a preferred embodiment arginase is provided as a PEGylated arginase prepared as described above; asparaginase can also be provided in PEGylated form. As noted above, reduction of glutamine through the use of aminotransferase inhibitors is also believed by the Inventors to be useful in reducing the growth of cancer cells. As such, an arginase/asparaginase treatment protocol as described above can include use of an aminotransferase inhibitor effective to reduce blood concentrations of glutamine (such as aminooxyacetate or AOA, 6-diazo-5-oxo-L-norleucine, azaserine, and/or acivicin).

REFERENCES

Balasubramanian, M. N., E. A. Butterworth, et al. (2013). "Asparagine synthetase: regulation by cell stress and involvement in tumor biology." Am J Physiol Endocrinol Metab 304(8): E789-799.

Bar-Peled, L., L. D. Schweitzer, et al. (2012). "Ragulator is a GEF for the rag GTPases that signal amino acid levels to mTORC1." Cell 150(6): 1196-1208.

Carroll, B., D. Maetzel, et al. (2016). "Control of TSC2-Rheb signaling axis by arginine regulates mTORC1 activity." Elife 5.

Chantranupong, L., S. M. Scaria, et al. (2016). "The CASTOR Proteins Are Arginine Sensors for the mTORC1 Pathway." Cell 165(1): 153-164.

Cheng, P. N., T. L. Lam, et al. (2007). "Pegylated recombinant human arginase (rhArg-peg5,000 mw) inhibits the in vitro and in vivo proliferation of human hepatocellular carcinoma through arginine depletion." Cancer Res 67(1): 309-317.

Chou, T. C. (2010). "Drug combination studies and their synergy quantification using the Chou-Talalay method." Cancer Res 70(2): 440-446.

Feun, L., M. You, et al. (2008). "Arginine deprivation as a targeted therapy for cancer." Curr Pharm Des 14(11): 1049-1057.

Gjymishka, A., N. Su, et al. (2009). "Transcriptional induction of the human asparagine synthetase gene during the unfolded protein response does not require the ATF6 and IRE1/XBP1 arms of the pathway." Biochem J 417(3): 695-703.

Guerrini, L., S. S. Gong, et al. (1993). "Cis- and trans-acting elements involved in amino acid regulation of asparagine synthetase gene expression." Mol Cell Biol 13(6): 3202-3212.

Hensley, C. T., A. T. Wasti, et al. (2013). "Glutamine and cancer: cell biology, physiology, and clinical opportunities." J Clin Invest 123(9): 3678-3684.

Horowitz, B. and A. Meister (1972). "Glutamine-dependent asparagine synthetase from leukemia cells. Chloride dependence, mechanism of action, and inhibition." J Biol Chem 247(20): 6708-6719.

Korangath, P., W. W. Teo, et al. (2015). "Targeting Glutamine Metabolism in Breast Cancer with Aminooxyacetate." Clin Cancer Res 21(14): 3263-3273.

Krall, A. S., S. Xu, et al. (2016). "Asparagine promotes cancer cell proliferation through use as an amino acid exchange factor." Nat Commun 7: 11457.

Lam, T. L., G. K. Wong, et al. (2009). "Recombinant human arginase inhibits proliferation of human hepatocellular carcinoma by inducing cell cycle arrest." Cancer Lett 277(1): 91-100.

Liu, R. Y., Z. Dong, et al. (2013). "Overexpression of asparagine synthetase and matrix metalloproteinase 19 confers cisplatin sensitivity in nasopharyngeal carcinoma cells." Mol Cancer Ther 12(10): 2157-2166.

Richards, N. G. and M. S. Kilberg (2006). "Asparagine synthetase chemotherapy." Annu Rev Biochem 75: 629-654.

Saxton, R. A., L. Chantranupong, et al. (2016). "Mechanism of arginine sensing by CASTOR1 upstream of mTORC1." Nature 536(7615): 229-233.

Su, N., Y. X. Pan, et al. (2008). "Correlation between asparaginase sensitivity and asparagine synthetase protein content, but not mRNA, in acute lymphoblastic leukemia cell lines." Pediatr Blood Cancer 50(2): 274-279.

Tsui, S. M., W. M. Lam, et al. (2009). "Pegylated derivatives of recombinant human arginase (rhArg1) for sustained in vivo activity in cancer therapy: preparation, characterization and analysis of their pharmacodynamics in vivo and in vitro and action upon hepatocellular carcinoma cell (HCC)." Cancer Cell Int 9: 9.

Wang, S., Z. Y. Tsun, et al. (2015). "Metabolism. Lysosomal amino acid transporter SLC38A9 signals arginine sufficiency to mTORC1." Science 347(6218): 188-194.

Wise, D. R. and C. B. Thompson (2010). "Glutamine addiction: a new therapeutic target in cancer." Trends Biochem Sci 35(8): 427-433.

Yang, H., X. He, et al. (2014). "Down-regulation of asparagine synthetase induces cell cycle arrest and inhibits cell proliferation of breast cancer." Chem Biol Drug Des 84(5): 578-584.

Zheng, L., W. Zhang, et al. (2016). "Recent Advances in Understanding Amino Acid Sensing Mechanisms that Regulate mTORC1." Int J Mol Sci 17(10).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of selectively inhibiting a cancer cell having low asparaginase expression, comprising:
   introducing an arginase to a media in contact with the cancer cell to reduce arginine concentration in the media to a concentration effective to inhibit growth of the cancer cell; and
   introducing an asparaginase to the media to reduce asparagine concentration in the media to a concentration effective to inhibit growth of the cancer cell,
   wherein the arginase and the asparaginase in combination provide a synergistic effect in reducing viability of the cancer cell, wherein the synergistic effect exceeds additive effects of monotherapies with the arginase and the asparaginase in inhibition of growth of the cancer cell having low asparaginase expression.

2. The method of claim 1, comprising reducing glutamine concentration in the media.

3. The method of claim 2, comprising supplying an aminotransferase inhibitor to reduce the glutamine concentration.

4. The method of claim 1, wherein the cancer cell is a breast cancer cell.

* * * * *

SEQUENCE LISTING

```
<160> NUMBER OF SEQ ID NOS: 19

<210> SEQ ID NO 1
<211> LENGTH: 323
<212> TYPE: PRT
<213> ORGANISM: Artificial Sequence
<220> FEATURE:
<223> OTHER INFORMATION: Mutation of human arginase 1, with deletion of
      N-terminal methionine.

<400> SEQUENCE: 1

Glu Gln Ser Ala Lys Ser Arg Thr Ile Gly Ile Ile Gly Ala Pro Phe
1               5                   10                  15

Ser Lys Gly Gln Pro Arg Gly Gly Val Glu Glu Gly Pro Thr Val Leu
            20                  25                  30

Arg Lys Ala Gly Leu Leu Glu Lys Leu Lys Glu Gln Glu Cys Asp Val
        35                  40                  45

Lys Asp Tyr Gly Asp Leu Pro Phe Ala Asp Ile Pro Asn Asp Ser Pro
    50                  55                  60

Phe Gln Ile Val Lys Asn Pro Arg Ser Val Gly Lys Ala Ser Glu Gln
65                  70                  75                  80

Leu Ala Gly Lys Val Ala Glu Val Lys Lys Asn Gly Arg Ile Ser Leu
                85                  90                  95

Val Leu Gly Gly Asp His Ser Leu Ala Ile Gly Ser Ile Ser Gly His
```

```
            100                 105                 110
Ala Arg Val His Pro Asp Leu Gly Val Ile Trp Val Asp Ala His Thr
            115                 120                 125

Asp Ile Asn Thr Pro Leu Thr Thr Thr Ser Gly Asn Leu His Gly Gln
        130                 135                 140

Pro Val Ser Phe Leu Leu Lys Glu Leu Lys Gly Lys Ile Pro Asp Val
145                 150                 155                 160

Pro Gly Phe Ser Trp Val Thr Pro Ser Ile Ser Ala Lys Asp Ile Val
                165                 170                 175

Tyr Ile Gly Leu Arg Asp Val Asp Pro Gly Glu His Tyr Ile Leu Lys
            180                 185                 190

Thr Leu Gly Ile Lys Tyr Phe Ser Met Thr Glu Val Asp Arg Leu Gly
        195                 200                 205

Ile Gly Lys Val Met Glu Glu Thr Leu Ser Tyr Leu Leu Gly Arg Lys
    210                 215                 220

Lys Arg Pro Ile His Leu Ser Phe Asp Val Asp Gly Leu Asp Pro Ser
225                 230                 235                 240

Phe Thr Pro Ala Thr Gly Thr Pro Val Val Gly Gly Leu Thr Tyr Arg
                245                 250                 255

Glu Gly Leu Tyr Ile Thr Glu Glu Ile Tyr Lys Thr Gly Leu Leu Ser
            260                 265                 270

Gly Leu Asp Ile Met Glu Val Asn Pro Ser Leu Gly Lys Thr Pro Glu
        275                 280                 285

Glu Val Thr Arg Thr Val Asn Thr Ala Val Ala Ile Thr Leu Ala Ser
    290                 295                 300

Phe Gly Leu Ala Arg Glu Gly Asn His Lys Pro Ile Asp Tyr Leu Asn
305                 310                 315                 320

Pro Pro Lys

<210> SEQ ID NO 2
<211> LENGTH: 13
<212> TYPE: PRT
<213> ORGANISM: Artificial Sequence
<220> FEATURE:
<223> OTHER INFORMATION: human arginase peptide/fragment

<400> SEQUENCE: 2

Ser Arg Thr Ile Gly Ile Ile Gly Ala Pro Phe Ser Lys
1               5                   10

<210> SEQ ID NO 3
<211> LENGTH: 16
<212> TYPE: PRT
<213> ORGANISM: Artificial Sequence
<220> FEATURE:
<223> OTHER INFORMATION: human arginase peptide/fragment

<400> SEQUENCE: 3

Gly Gln Pro Arg Gly Gly Val Glu Glu Gly Pro Thr Val Leu Arg Lys
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: human arginase peptide/fragment

<400> SEQUENCE: 4
```

```
Ala Gly Leu Leu Glu Lys
1               5

<210> SEQ ID NO 5
<211> LENGTH: 7
<212> TYPE: PRT
<213> ORGANISM: Artificial Sequence
<220> FEATURE:
<223> OTHER INFORMATION: human arginase peptide/fragment

<400> SEQUENCE: 5

Glu Gln Glu Cys Asp Val Lys
1               5

<210> SEQ ID NO 6
<211> LENGTH: 20
<212> TYPE: PRT
<213> ORGANISM: Artificial Sequence
<220> FEATURE:
<223> OTHER INFORMATION: human arginase peptide/fragment

<400> SEQUENCE: 6

Asp Tyr Gly Asp Leu Pro Phe Ala Asp Ile Pro Asn Asp Ser Pro Phe
1               5                   10                  15

Gln Ile Val Lys
            20

<210> SEQ ID NO 7
<211> LENGTH: 7
<212> TYPE: PRT
<213> ORGANISM: Artificial Sequence
<220> FEATURE:
<223> OTHER INFORMATION: human arginase peptide/fragment

<400> SEQUENCE: 7

Asn Pro Arg Ser Val Gly Lys
1               5

<210> SEQ ID NO 8
<211> LENGTH: 8
<212> TYPE: PRT
<213> ORGANISM: Artificial Sequence
<220> FEATURE:
<223> OTHER INFORMATION: human arginase peptide/fragment

<400> SEQUENCE: 8

Ala Ser Glu Gln Leu Ala Gly Lys
1               5

<210> SEQ ID NO 9
<211> LENGTH: 5
<212> TYPE: PRT
<213> ORGANISM: Artificial Sequence
<220> FEATURE:
<223> OTHER INFORMATION: human arginase peptide/fragment

<400> SEQUENCE: 9

Val Ala Glu Val Lys
1               5

<210> SEQ ID NO 10
<211> LENGTH: 61
<212> TYPE: PRT
<213> ORGANISM: Artificial Sequence
<220> FEATURE:
<223> OTHER INFORMATION: human arginase peptide/fragment
```

```
<400> SEQUENCE: 10

Asn Gly Arg Ile Ser Leu Val Leu Gly Gly Asp His Ser Leu Ala Ile
1               5                   10                  15

Gly Ser Ile Ser Gly His Ala Arg Val His Pro Asp Leu Gly Val Ile
            20                  25                  30

Trp Val Asp Ala His Thr Asp Ile Asn Thr Pro Leu Thr Thr Thr Ser
        35                  40                  45

Gly Asn Leu His Gly Gln Pro Val Ser Phe Leu Leu Lys
    50                  55                  60

<210> SEQ ID NO 11
<211> LENGTH: 17
<212> TYPE: PRT
<213> ORGANISM: Artificial Sequence
<220> FEATURE:
<223> OTHER INFORMATION: human arginase peptide/fragment

<400> SEQUENCE: 11

Ile Pro Asp Val Pro Gly Phe Ser Trp Val Thr Pro Ser Ile Ser Ala
1               5                   10                  15

Lys

<210> SEQ ID NO 12
<211> LENGTH: 19
<212> TYPE: PRT
<213> ORGANISM: Artificial Sequence
<220> FEATURE:
<223> OTHER INFORMATION: human arginase peptide/fragment

<400> SEQUENCE: 12

Asp Ile Val Tyr Ile Gly Leu Arg Asp Val Asp Pro Gly Glu His Tyr
1               5                   10                  15

Ile Leu Lys

<210> SEQ ID NO 13
<211> LENGTH: 5
<212> TYPE: PRT
<213> ORGANISM: Artificial Sequence
<220> FEATURE:
<223> OTHER INFORMATION: human arginase peptide/fragment

<400> SEQUENCE: 13

Thr Leu Gly Ile Lys
1               5

<210> SEQ ID NO 14
<211> LENGTH: 14
<212> TYPE: PRT
<213> ORGANISM: Artificial Sequence
<220> FEATURE:
<223> OTHER INFORMATION: human arginase peptide/fragment

<400> SEQUENCE: 14

Tyr Phe Ser Met Thr Glu Val Asp Arg Leu Gly Ile Gly Lys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: human arginase peptide/fragment

<400> SEQUENCE: 15
```

Val Met Glu Glu Thr Leu Ser Tyr Leu Leu Gly Arg Lys
1               5                   10

<210> SEQ ID NO 16
<211> LENGTH: 42
<212> TYPE: PRT
<213> ORGANISM: Artificial Sequence
<220> FEATURE:
<223> OTHER INFORMATION: humsn arginase peptide/fragment

<400> SEQUENCE: 16

Arg Pro Ile His Leu Ser Phe Asp Val Asp Gly Leu Asp Pro Ser Phe
1               5                   10                  15

Thr Pro Ala Thr Gly Thr Pro Val Val Gly Leu Thr Tyr Arg Glu
            20                  25                  30

Gly Leu Tyr Ile Thr Glu Glu Ile Tyr Lys
        35                  40

<210> SEQ ID NO 17
<211> LENGTH: 18
<212> TYPE: PRT
<213> ORGANISM: Artificial Sequence
<220> FEATURE:
<223> OTHER INFORMATION: human arginase peptide/fragment

<400> SEQUENCE: 17

Thr Gly Leu Leu Ser Gly Leu Asp Ile Met Glu Val Asn Pro Ser Leu
1               5                   10                  15

Gly Lys

<210> SEQ ID NO 18
<211> LENGTH: 29
<212> TYPE: PRT
<213> ORGANISM: Artificial Sequence
<220> FEATURE:
<223> OTHER INFORMATION: human argiinase peptide/fragment

<400> SEQUENCE: 18

Thr Pro Glu Glu Val Thr Arg Thr Val Asn Thr Ala Val Ala Ile Thr
1               5                   10                  15

Leu Ala Ser Phe Gly Leu Ala Arg Glu Gly Asn His Lys
            20                  25

<210> SEQ ID NO 19
<211> LENGTH: 9
<212> TYPE: PRT
<213> ORGANISM: Artificial Sequence
<220> FEATURE:
<223> OTHER INFORMATION: human arginase peptide/fragment

<400> SEQUENCE: 19

Pro Ile Asp Tyr Leu Asn Pro Pro Lys
1               5